US 8,492,114 B2

(12) United States Patent
Thompson et al.

(10) Patent No.: US 8,492,114 B2
(45) Date of Patent: Jul. 23, 2013

(54) METHODS OF COMBINED BIOPROCESSING AND RELATED MICROORGANISMS, THERMOPHILIC AND/OR ACIDOPHILIC ENZYMES, AND NUCLEIC ACIDS ENCODING SAID ENZYMES

(75) Inventors: David N. Thompson, Idaho Falls, ID (US); William A. Apel, Jackson, WY (US); Vicki S. Thompson, Idaho Falls, ID (US); Thomas E. Ward, Furnace, PA (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 215 days.

(21) Appl. No.: 12/587,229

(22) Filed: Oct. 2, 2009

(65) Prior Publication Data

US 2011/0081683 A1 Apr. 7, 2011

Related U.S. Application Data

(63) Continuation-in-part of application No. 12/322,359, filed on Jan. 29, 2009, now Pat. No. 7,858,353, which is a continuation-in-part of application No. 12/380,551, filed on Feb. 26, 2009, application No. 12/587,229, which is a continuation-in-part of application No. 12/380,450, filed on Feb. 26, 2009, application No. 12/587,229, which is a continuation-in-part of application No. 12/380,554, filed on Feb. 26, 2009, now Pat. No. 7,960,534, application No. 12/587,229, which is a continuation-in-part of application No. 12/380,008, filed on Feb. 20, 2009, application No. 12/587,229, which is a continuation-in-part of application No. 12/321,636, filed on Jan. 23, 2009, now Pat. No. 7,923,234.

(60) Provisional application No. 61/025,136, filed on Jan. 31, 2008, provisional application No. 61/032,339, filed on Feb. 28, 2008, provisional application No. 61/031,984, filed on Feb. 27, 2008, provisional application No. 61/031,593, filed on Feb. 26, 2008, provisional application No. 61/030,820, filed on Feb. 22, 2008, provisional application No. 61/023,639, filed on Jan. 25, 2008.

(51) Int. Cl.
*C12P 1/00* (2006.01)
*C12S 3/00* (2006.01)
*C12N 1/00* (2006.01)
*C12N 9/00* (2006.01)

(52) U.S. Cl.
USPC .................. 435/41; 435/252.3; 435/254.11; 435/183; 435/209; 435/72; 435/267

(58) Field of Classification Search
None
See application file for complete search history.

(56) References Cited

U.S. PATENT DOCUMENTS

| | | | |
|---|---|---|---|
| 4,237,226 A | 12/1980 | Grethlein |
| 4,581,333 A | 4/1986 | Kourilsky et al. |
| 4,624,922 A | 11/1986 | Horikoshi et al. |
| 5,098,825 A | 3/1992 | Tchen et al. |
| 5,882,905 A | 3/1999 | Saha et al. |
| 5,916,795 A | 6/1999 | Fukunaga et al. |
| 5,948,667 A | 9/1999 | Cheng et al. |
| 6,083,733 A | 7/2000 | Gronberg et al. |
| 6,268,197 B1 | 7/2001 | Schulein et al. |
| 6,426,211 B1 | 7/2002 | De Buyl et al. |
| 6,506,585 B2 | 1/2003 | Danielsen et al. |
| 6,777,212 B2 | 8/2004 | Asakura et al. |
| 6,833,259 B2 | 12/2004 | Bhosle et al. |
| 7,727,755 B2 | 6/2010 | Thompson |
| 2003/0134395 A1 | 7/2003 | Shetty |
| 2003/0233674 A1 | 12/2003 | Gabor |
| 2003/0233675 A1 | 12/2003 | Cao et al. |
| 2004/0029129 A1 | 2/2004 | Wang et al. |
| 2005/0112742 A1 | 5/2005 | Thompson et al. |

(Continued)

FOREIGN PATENT DOCUMENTS

| | | |
|---|---|---|
| DE | 197 17 893 A1 | 1/1999 |
| WO | 81/00577 | 3/1981 |
| WO | 99/06584 A1 | 2/1999 |
| WO | 03/068926 | 8/2003 |
| WO | WO 2005/066339 * | 7/2005 |
| WO | 2006/117247 A1 | 11/2006 |
| WO | 2010/014976 A2 | 2/2010 |

OTHER PUBLICATIONS

Eckert et al. Thermoacidophilic endoglucanase from *Alicyclobacillus acidocaldarius* displays high sequence similarity to arbinofuranosidase belonging to family 51 of glycosidase hydrolases. Eur. J. Biochem. (2003) 270 3593-3602.*

(Continued)

*Primary Examiner* — Nashaat Nashed
(74) *Attorney, Agent, or Firm* — TraskBritt

(57) ABSTRACT

A genetically modified organism comprising: at least one nucleic acid sequence and/or at least one recombinant nucleic acid isolated from *Alicyclobacillus acidocaldarius* and encoding a polypeptide involved in at least partially degrading, cleaving, transporting, metabolizing, or removing polysaccharides, cellulose, lignocellulose, hemicellulose, lignin, starch, sugars, sugar oligomers, carbohydrates, complex carbohydrates, chitin, heteroxylans, glycosides, xylan-, glucan-, galactan-, or mannan-decorating groups; and at least one nucleic acid sequence and/or at least one recombinant nucleic acid encoding a polypeptide involved in fermenting sugar molecules to a product. Additionally, enzymatic and/or proteinaceous extracts may be isolated from one or more genetically modified organisms. The extracts are utilized to convert biomass into a product. Further provided are methods of converting biomass into products comprising: placing the genetically modified organism and/or enzymatic extracts thereof in fluid contact with polysaccharides, cellulose, lignocellulose, hemicellulose, lignin, starch, sugars, sugar oligomers, carbohydrates, complex carbohydrates, chitin, heteroxylans, glycosides, and/or xylan-, glucan-, galactan-, or mannan-decorating groups.

13 Claims, No Drawings

U.S. PATENT DOCUMENTS

| | | | |
|---|---|---|---|
| 2006/0105442 A1* | 5/2006 | Wu et al. | 435/161 |
| 2006/0211083 A1 | 9/2006 | Katzen et al. | |
| 2007/0082381 A1 | 4/2007 | Wilting et al. | |
| 2007/0134778 A1 | 6/2007 | Benning et al. | |
| 2007/0148728 A1 | 6/2007 | Johnson et al. | |
| 2009/0203107 A1* | 8/2009 | Thompson et al. | 435/202 |
| 2009/0215168 A1 | 8/2009 | Lee et al. | |
| 2009/0221049 A1 | 9/2009 | Shaw et al. | |
| 2009/0226978 A1 | 9/2009 | Thompson et al. | |
| 2009/0253205 A1 | 10/2009 | Thompson et al. | |
| 2009/0263859 A1 | 10/2009 | Thompson et al. | |
| 2009/0269827 A1 | 10/2009 | Thompson et al. | |
| 2010/0203583 A1 | 8/2010 | Thompson et al. | |
| 2010/0311110 A1 | 12/2010 | Thompson et al. | |
| 2011/0275135 A1 | 11/2011 | Lee et al. | |

OTHER PUBLICATIONS

Yuan et al., Expression of acidophilic alpha-amylase from *Alicyclobacillus acidocaldarius*, Sheng Wu Gong Cheng Xue Bao, Jan. 2005, 21(1):78-83. Abstract only.

PCT International Search Report and Written Opinion of the International Searching Authority for PCT/US10/51095, dated Dec. 2, 2010, 11 pages.

Uhl et al., "The first description of an archaeal hemicellulase: the xylanase from *Thermococcus zillgii* strain AN1," Extremophiles (1999) 3:263-267.

Uniprot Direct submission Q9RHZ5_ALIAC, "Putative maltose transport membrane protein malF," Nov. 13, 2007. [Retrieved from the Internet Jan. 22, 2010: <http://www.uniprot.org/uniprot/Q9RHZ5.txt?version=30?].

UniProtKB/TrEMBL Q9JRQ1 [online]. Oct. 1, 2000. Available on the internet at <<URL://http://www.uniprot.org/uniprot/Q9JRQ1>>.

Upreti et al., 2003, Bacterial glycoproteins: Functions, biosynthesis and applications. Proteomics, 3: 363-379.

Urdea, M. S., 1988, Nucleic Acids Research, II: 4937-4957.

Vieille and Zeikus, 2001, Micro. and Mol. Biol. Rev., vol. 65, No. 1, p. 1-43.

Viikari et al., "Xylanases in bleaching: From an idea to the industry." FEMS Microbiology Reviews 13 (1994).

Walker, G. T. et al., 1992, NAR 20: 1691-1696.

Walker, G.T. et al., 1992, PNAS. USA, 89:392-396.

Walseth, Curtis S., Occurrence of Cellulases in Enzyme Preparations from Microorganisms, TAPPI vol. 35, No. 5, May 1952, pp. 228-233.

Ward et al., "Characterization of a new bacteriophage which infects bacteria of the genus *Acidiphilium*," Journal of General Virology (1993) 74: 2419-2425.

Ward et al., "Electrotransformation of Acidophilic, Heterotrophic, Gram-negative Bacteria," Electrotransformation of Bacteria, Natalie Eynard, Justin Teissie (eds.), Springer (2000) pp. 94-103.

Whisstock et al. "Prediction of Protein Function from Protein Sequence and Structure" Quarlty Reviews of Biophysics 36, 3 (2003) pp. 307-340 (35 pages).

Witkowski et al. "Conversion of a β-Ketoacyl Synthase to a Malonyl Decarboxylase by Replacement of the Active-Site Cysteine with Glutamine" American Chemical Society, Biochemistry, vol. 38, No. 36, 1999 pp. 11643-11650 (8 pages).

Wright et al., "Ethanol from Biomass by Enzymatic Hydrolysis," Chemical Engineering Progress, Aug. 1988, pp. 62-74.

Lin et al., "Purification, Characterization, and Gene Cloning of Thermopsin, a Thermostable Acid Protease from *Sulfolobus acidocaldarius*," The Journal of Biological Chemistry, 1990, vol. 265, No. 3, pp. 1490-1495.

Aden et al., "Lignocellulosic Biomass to Ethanol Process Design and Economics Utilizing Co-Current Dilute Acid Prehydrolysis and Enzymatic Hydrolysis for Corn Stover," NREL/TP-510-32438, National Renewable Energy Laboratory, Golden Colorado. Jun. 2002, pp. 1-88.

Avella et al., "A New Class of Biodegradable Materials: Poly-3-hydroxy-butyrate/Steam Exploded Straw Fiber Composites. I. Thermal and Impact Behaviour," Journal of Applied Polymer Science, vol. 49, 2091-2103 (1993).

Badger, P.C., "Ethanol from cellulose: A general review," In: J. Janick and A. Whipkey (eds.), Trands in new crops and new uses. ASHS Press, Alexandria, VA, 2002, pp. 17-21.

Bailey et al., "Interlaboratory testing of methods for assay of xylanase activity," Journal of Biotechnology, 23 (1992) 257-270.

Barany, F., 1991, PNAS. USA, 88: 189-193.

Bergquist et al., "Molecular diversity of thermophilic cellulolytic and hemicellulolytic bacteria," FEMS Microbiology Ecology 28 (1999) 99-110.

Bertoldo et al., 2004, Eng. Life Sci., 4, No. 6.

Bhatia et al., "Microbial beta-Glucosidases: Cloning, Properties, and Applications," Critical Reviews in Biotechnology, 22(4):375-407, Jan. 1, 2002.

Bork, Peer, "Powers and Pitfalls in Sequence Analysis: The 70% Hurdle," Genome Research, 2000, 10:398-400.

Borman, S., 2006, Glycosylation Engineering. Chem. Eng. News, 84(36): 13-22.

Bowie et al., "Deciphering the Message in Protein Sequences: Tolerance to Amino Acid Substitutions," Science, 1990, 247:1306-1310.

Breves et al., "Genes Encoding Two Different beta-Glucosidases of *Thermoanaerobacter brockii* Are Clustered in a Common Operon," Applied and Environmental Microbiology, vol. 63, No. 10, Oct. 1997, pp. 3902-3910.

Broun et al. "Catalytic Plasticity of Fatty Acid Modification Enzymes Underlying Chemical Diversity of Plant Lipids" Science vol. 282 Nov. 13, 1998 pp. 1315-1317 (4 pages).

Buckholz, R. G., 1993, Yeast systems for the expression of heterologous gene products. Curr. Op. Biotechnology 4: 538-542.

Burg, J. L. et al., 1996, Mol. and Cell. Probes, 10: 257-271.

Chu, B. C. F. et al., 1986, NAR, 14: 5591-5603.

Collins et al., "Xylanaes, Xylanase Families and Extremophilic Xylanses," FEMS Microbiology Review, 2005, pp. 3-23.

Cowling, Ellis B., "Physical and Chemical Constrains in the Hydrolysis of Cellulose and Lignocellulosic Materials," Biotechnol. & Bioeng. Symposium No. 5, 163-181 (1975).

Crout et al., "Glycosidases and glycosyl transferases in glycoside and oligosaccharide synthesis," Current Opinion in Chemical Biology, Current Biology Ltd, London, GB, vol. 2, No. 1, Feb. 1, 1998, pp. 98-111.

Dale, M. Clark, "Enzymatic simultaneous saccharification and fermentation (SSF) of biomass to ethanol in a pilot 130 liter multistage continuous reactor separator," Bio-Process Innovation, Inc., W. Lafayette, IN, 2005, 10 pages.

Database EMBL [Online]. Mar. 16, 2007. XP-002627757. Database accession No. ER073884, 1 page.

Database Geneseq [Online]. May 21, 1998. XP-002627734. Database accession No. AAW35004, 1 page.

Database UniProt [Online]. May 1, 1997. XP-002630045. Database accession No. P96090, 1 page.

Database UniProt [Online]. Oct. 1, 2001. XP-002627736. Database accession No. Q97Ul4, 1 page.

Database UniProt [Online]. Feb. 10, 2009. XP-000002659383. Database accession No. B7DT70, 1 page.

Database UniProt [Online]. Jun. 26, 2007. XP-002627735. Database accession No. A5IKZ4, 1 page.

Database UniProt [Online]. Nov. 3, 2009. XP-002627733. Database accession No. C8WTP2, 1 page.

Devos et al. "Practical Limits of Functiona Prediction" Proteins: Structure, Function, and Genetics 41 (2000) pp. 98-107 (10 pages).

Duck, P. et al., 1990, Biotechniques, 9: 142-147.

Eckert et al., "Gene cloning, sequencing, and characterization of a family 9 endoglucanase (CelA) with an unusual pattern of activity from the thereomoacidophile *Alicyclobacillus acidocaldarius* ATCC27009," Applied Microbiology and Biotechnology, vol. 60, pp. 428-436 (2002).

Eckert, Kelvin, "Dissertation, Cloning and Characterization of two glycosidases from the acidothermophile *Alicyclobacillus acidocaldarius* ATCC27009," Berlin, Sep. 17, 2003, 113 pages.

Edwards, C. P., and Aruffo, A., 1993, Current applications of COS cell based transient expression systems. Curr. Op. Biotechnology 4: 558-563.

Ehrman, Tina, "Standard Method for Determination of Total Solids in Biomass," Chemical Analysis and Testing Task, Laboratory Analytical Procedure, Oct. 28, 1994, 242 total pages.

EMBL Submission CP001728, Sep. 2009. [Retrieved from the Internet: URL:http://www.ebi.ac.uk/Tools/dbfetch/embifetch?style=html&id=CP001728&Submit=Go], 51 pages.

Erlich, H.A., J Clin. Immunol., Nov. 1989; 9(6):437-47.

Extended Supplementary European Search Report for EP 09 70 3173, dated Apr. 20, 2011, 7 pages.

Extended Supplementary European Search Report for EP 09 82 3952, dated Sep. 20, 2011, 7 pages.

Fan et al., "The Nature of Lignocellulosics and Their Pretreatments for Enzymatic Hydrolysis," Advances in Biochemical Engineering/Biotechnology, 1982, vol. 23/1982, 157-187.

Flanagan, et al., "Development of gas phase bioreactors for the removal of nitrogen oxides from synthetic flue gas streams," Fuel 81 (2002) 1953-1961.

Fushinobu et al., "Crystallographic and mutational analyses of an extremely acidophilic and acid-stable xylanase: biased distribution of acidic residues and importance of Asp37 for catalysis at low pH," Protein Engineering vol. 11, No. 12, pp. 1121-1128, 1998.

Garrote, G, H Dominguez, and JC Parajo, 2001, Manufacture of xylose-based fermentation media from corncobs by posthydrolysis of autohydrolysis liquors, Appl. Biochem. Biotechnol., 95:195-207.

GenBank: E17054.1 Direct Submission *Alicyclobacillus acidocaldarius* genomic DNA clone pOP3 containing acyl carrier protein gene. Nov. 5, 2005 [Retrieved from the Internet Jan. 23, 2010: http://www.ncbi.nlm.nih.gov/nuccore/E17054.1?ordinalpos=2&tool=Entr.

Gessesse, Amare, "Purification and Properties of Two Thermostable Alkaline Xylanases from an *Alkaliphilic bacillus* sp.," Applied and Environmental Microbiology, Sep. 1998, pp. 3533-3535.

Glenn et al., "Transformation of Acidiphilium by electroporation and conjugation," Can J Microbiol. May 1992;38 (5):387-93.

Goldstein et al., "The Hydrolysis of Cellulose with Superconcentrated Hydrochloric Acid," Biotechnology and Bioengineering Symp. No. 13, pp. 17-25 (1983).

Grassin et al., "Chapter 2.13, Fruit Juices," (T. Godfrey and S. West, eds.), Industrial Enzymology, 2nd Ed., pp. 227-264 (1996).

Grethlein, H. E., "Pretreatment for enhanced hydrolysis of cellulosic biomass," Biotechnol. Adv. 1984. 2:43-62.

Grethlein, Hans E., "Comparison of the Economics of Acid and Enzymatic Hydrolysis of Newsprint," Biotechnology and Bioengineering, vol. XX, pp. 503-525 (1978).

Guateli, J. C. et al., 1990, PNAS. USA, 87: 1874-1878.

Hamelinck, CN, G van Hooijdonk, and APC Faaij, 2005, Ethanol from lignocellulosic biomass: techno-economics performance in short-, middle-, and long-term, Biomass Bioenergy, 28:384-410.

Hanselmann, K.W., "Lignochemicals," Experientia 38 (1982) pp. 176-189.

Houghton et al., "Fungal Upgrading of Wheat Straw for Straw-Thermoplastics Production," Applied Biochemistry and Biotechnology, vol. 113-116, 2004, pp. 71-93.

Hulsmann et al., "Maltose and maltodextrin transport in the thermoacidophilic gram-positive bacterium *Alicyclobacillus acidocaldarius* is mediated by a high-affinity transport system that includes a maltose binding protein tolerant to low pH," J. Bacteriology, Nov. 2000, p. 6292-6301.

Huygen, K. et al., 1996, Nature Medicine, 2(8): 893-898.

International Preliminary Report on Patentability and Written Opinion of the International Searching Authority for PCT/US06/42566 dated Apr. 23, 2009 (7 pages).

International Search Report and Written Opinion of the International Search Authority for PCT/US09/32333, mailed Jun. 19, 2009, 9 pages.

International Search Report of the International Searching Authority for PCT/US06/42566, dated Jul. 25, 2008.

Ito et al., "Purification and properties of acid stable xylanases from *Aspergillus kawachii*," Bioscience Biotechnology and Biochemistry 56 (4):547-550, Apr. 1992.

Jeffries, 1996, Curr. Op. in Biotech., 7:337-342.

Jones et al., "Cloning and transcriptional analysis of the *Thermoanaerobacter ethanolicus* strain 39E maltose ABC transport system," Extremophiles 2002, 6:291-299.

Kenealy et al., "Rapid 2,2'-bicinchoninic-based xylanase assay compatible with high throughput screening," Biotechnology Letters 25: 1619-1623, 2003.

Kievitis, T. et al., 1991, J. Virol. Methods, 35: 273-286.

Knappert et al., "Partial Acid Hydrolysis of Cellulosic Materials as a Pretreatment for Enzymatic Hydrolysis," Biotechnology and Bioengineering, vol. XXII, pp. 1449-1463 (1980).

Kohler, G. et al., 1975, Nature, 256(5517): 495497.

Kulkarni et al., "Molecular and biotechnological aspects of xylanases," FEMS Microbiology Reviews 23 (1999) 411-456.

Kwoh, D.Y. et al., 1989, PNAS. USA, 86: 1173-1177.

Lau et al., "PCR ligation mutagenesis in transformable *Streptococci*: application and efficiency," Journal of Microbiological Methods 49 (2002) 193-205.

Lauro et al., "Characterization of a β-glycosidase from the thermoacidophilic bacterium *Alicyclobacillus acidocaldarius*," Extremophiles (2006) 10:301-310.

Lauro et al., "Isolation and characterization of a new family 42 beta-galactosidase from the thermoacidophilic bacterium *Alicyclobacillus acidocaldarius*: Identification of the active site residues," Biochimica et Biophysica Acta 1784 (2008) 292-301.

Lavarack et al., "The acid hydrolysis of sugarcane begasse hemicellulose to produce xylose, arabinose, glucose and other products," Biomass and Bioenergy 23 (2002) 367-380.

Lee et al., "Oxygen Effects on Thermophilic Microbial Populations in Biofilters Treating Nitric Oxide Containing Off-Gas Streams," Environmental Progress, vol. 20, No. 3, Oct. 2001.

Liu C, and CE Wyman, 2003, The effect of flow rate of compressed hot water on xylan, lignin, and total mass removal from corn stover, Ind. Eng. Chem. Res., 42:5409-5416.

Lucas et al., C4-Dicarboxylate Transporter/Malic Acid Transport Protein [*Alicyclobacillus acidocaldarius* LAA1], GenBank Direct Submission, Accession No. EED06059, Dec. 17, 2008 (Retrieved from the Internet Dec. 15, 2009: <URL:http://www.ncbl.nlm.nlh.gov/.

Luckow, V. A., 1993, Baculovirus systems for the expression of human gene products. Curr. Op. Biotechnology 4: 564-572.

Lynd et al., 2002, Micro. and Mol. Biol. Rev., vol. 66, No. 3, p. 506-577.

Lynd, Lee R., "Overview and Evaluation of Fuel Ethanol from Cellulosic Biomass: Technology, Economics, the Environment, and Policy," Annu. Rev. Energy Environ. 1996, 21:403-65.

MacKenzie et al., "Multiple Chromosomes in Bacteria: The Yin and Yang of trp Gene Localization in *Rhodobacter sphaeroides* 2.4.1," Genetics 153: 525-538 (Oct. 1999).

Malherbe and Cloete, 2002, Re/View in Environmental Science and Bio/Technology, 1: 105-114.

Manchenko, Gennady P., "Handbook of Detection of Enzymes on Electrophoretic Gels," CRC Press, Inc. 1994, pp. 220-240.

Matthews, J. A. et al., 1988, Anal. Biochem., 169: 1-25.

McCoy, Michael, "Chemical Makers Try Biotech Paths," Chemical Engineering News, Jun. 22, 1998, pp. 13-19.

Merrifield, R. D., 1966, J. Am. Chem. Soc., 88(21): 5051-5052.

Michel et al., "Specificity of the protein secretory apparatus: secretion of the heat-labile enterotoxin B subunit pentamers by different species of Gram bacteria," Gene 152 (1995) pp. 41-45.

Miele, E. A. et al., 1983, J. Mol. Biol., 171: 281-295.

Mielenz, 2001, Curr. Op. in Micro., 4:324-329.

Mosier et al., "Industrial Scale-Up of pH-Controlled Liquid Hot Water Pretreatment of Corn Fiber for Fuel Ethanol Production," Applied Biochemistry and Biotechnology, vol. 125, 2005, pp. 77-97.

Neddleman and Wunsch, J. Mol. Biol. 48: 443 (1970).

Ng et al., 1981, Applied and Environmental Microbiology, 41(6):1337-1343.

Ohta et al., "Purification and Characterization of an Acidophilic Xylanase from *Aureobasidium pullulans* var. melanigenum and Sequence Analysis of the Encoding Gene," Journal of Bioscience and Bioengineering, vol. 92, No. 3, 262-270, 2001.

Olins, P. O., and Lee, S. C., 1993, Recent advances in heterologous gene expression in *E. coli*. Curr. Op. Biotechnology 4: 520-525.

Ooshima et al., "Simultaneous saccharification and fermentation of cellulose: Effect of ethanol on enzymatic saccharification of cellulose," Department of Applied Chemistry, Faculty of Engineering, Osaka City University, Osaka 558, Japan, Jun. 5, 1984.
Pajunen et al., Microbiology (2005) 151, 1209-1218.
Patel et al., (2006), "Medium and long-term opportunities and risks of the biotechnological production of bulk chemicals from renewable resources: The potential of white biotechnology". The BREW Project. Final Report prepared under the European Commission's Growth Programme (DG Research), (publica.fraunhofer.de/eprints/N-48834.pdf).
PCT International Preliminary Report on Patentability of the International Search Authority for PCT/US09/32333, dated Aug. 3, 2010.
PCT International Preliminary Report on Patentability of the International Searching Authority for PCT/US09/00442, dated Jul. 27, 2010.
PCT International Preliminary Report on Patentability of the International Searching Authority for PCT/US09/34701, dated Aug. 24, 2010.
PCT International Preliminary Report on Patentability of the International Searching Authority for PCT/US09/35275, dated Aug. 31, 2010.
PCT International Preliminary Report on Patentability of the International Searching Authority for PCT/US09/35331, dated Aug. 31, 2010.
PCT International Preliminary Report on Patentability of the International Search Authority for PCT/US09/35307, mailed Jan. 25, 2011.
PCT International Search Report and Written Opinion of the International Search Authority for PCT/US11/34852, dated Oct. 21, 2011, 12 pages.
PCT International Search Report and Written Opinion of the International Searching Authority for PCT/US09/00442, dated May 18, 2009, 8 pages.
PCT International Search Report and Written Opinion of the International Searching Authority for PCT/US09/34701, dated Jan. 12, 2010, 10 pages.
PCT International Search Report and Written Opinion of the International Searching Authority for PCT/US09/35275, dated Feb. 25, 2010, 13 pages.
PCT International Search Report and Written Opinion of the International Searching Authority for PCT/US09/35331, dated Feb. 23, 2010, 10 pages.
PCT International Search Report and Written Opinion of the International Search Authority for PCT/US09/35307, dated Jun. 10, 2010, 10 pages.
PCT International Search Report and Written Opinion of the International Search Authority for PCT/US10/25521, dated Jul. 14, 2010, 12 pages.
PCT International Search Report of the International Search Authority for PCT/US10/25521 Jul. 14, 2010.
Pearson and Lipman, Proc. Natl. Acad. Sci. (U.S.A.) 85: 2444 (1988).
Perlack et al., "Biomass as Feedstock for a Bioenergy and Bioproducts Industry: The Technical Feasibility of a Billion-Ton Annual Supply," USDA and DOE, Apr. 2005, 78 pages.
Ragauskas et al., "The Path Forward for Biofuels and Biomaterials," Science, Jan. 27, 2006, vol. 311, pp. 484-4589.
Ramos et al., "Biomechanical and Biochemical Pulping of Sugarcane Bagasse with *Ceriporiopsis subvermispora* Fungal and Xylanase Pretreatments," J. Agric. Food Chem. 2001, 49, 1180-1186.
Saeman et al., "Quantitative Saccharification of Wood and Cellulose," Industrial and Engineering Chemistry, Jan. 1945, vol. 17, No. 1, pp. 35-37.
Saha et al., "Dilute Acid Pretreatment, Enzymatic Saccharification, and Fermentation of Rice Hulls to Ethanol," Biotechnol. Prog. 2005, 21, 816-822.
Sanchez-Pescador, R., 1988, J. Clin. Microbiol., 26(10): 1934-1938.
Sa-Pereira et al., "Rapid production of thermostable cellulose-free xylanase by a strain of *Bacillus subtilis* and its properties," Enzyme and Microbial Technology, 30 (2002) 924-933.

Schafer et al., "X-ray Structures of the Maltose-Maltodextrin-binding Protein of the Thermoacidophilic Bacterium *Alicyclobacillus acidocaldarius* Provide Insight into Acid Stability of Proteins," J. Mol. Biol. 2004, 335:261-274.
Schäffer, C. et al., 2001, Prokaryotic glycosylation. Proteomics, 1: 248-261.
Scheffel et al., "Functional reconstitution of a maltrose ATP-binding cassette transporter from the thermoacidophilic gram-positive bacterium *Alicyclobacillus acidocaldarius*," Biochem Biophy Acta, 2004, 1656(1):57-65.
Schell et al., "Dilute-Sulfuric Acid Pretreatment of Corn Stover in Pilot-Scale Reactor," Applied Biochemistry and Biotechnology, vol. 105-108, 2003, pp. 69-85.
Schneider, "Import of solutes by ABC transporters—the maltose system. ABC protein: from bacteria to man," Elsevier Science, London 2003, p. 157-185. [Retrieved from the Internet on Jan. 24, 2010; <http://www2.hu-berlin.de/biologie/baktphys/paper/1_ABC/r.
Schwarz, Wolfgang H., "A list of cellulolytic bacteria," Technische Universitat Munchen, Apr. 24, 2003, 8 pages.
Schwermann, B. et al., 1994, Purification, properties and structural aspects of a thermoacidophilic a-amylase from *Alicyclobacillus acidocaldarius* ATCC 27009, insight into acidostability of proteins. Eur. J. Biochem. 226: 981-991.
Seffernick et al. "Melamine Deaminase and Atrazine Chlorohydrolase: 98 Percent Identical but Functionally Different" Journal of Bacteriology vol. 183, No. 8, Apr. 2001 pp. 2045-2410 (6 pages).
Shallom et al., "Microbial hemicellulases," Current Opinion in Microbiology, Current Biology Ltd, GB, vol. 6, No. 3, Jun. 1, 2003, pp. 219-228.
Simpson et al., "An extremely Thermostable xylanase from the *Thermophilic eubacterium* Thermotoga," Biochem. J. (1991) 277, 413-417.
Smook, G.A., "Handbook for Pulp & Paper Technologists," Tappi Pr; 2nd Ed. (Jun. 1992) pp. 65-88.
Subramaniyan et al., "Cellulase-free xylanases from *Bacillus* and other microorganisms," FEMS Microbiology Letters 183 (2000) 1-7.
Sunna et al., "Glycosyl hydrolases from hyperthermophiles," Extremophiles (1997) 12-13.
Supplemental European Search Report for EP 06 82 7231, dated Nov. 12, 2009, 6 pages.
Techapun et al., "Production of a cellulose-free xylanase from agricultural waste materials by a thermotolerant *Streptomyces* sp.," Biotechnology Letters 23: 1685-1689, 2001.
Thompson et al., "Comparison of Pretreatment Methods on the Basis of Available Surface Area," Bioresource Technology 39 (1992) 155-163.
Thompson et al., "In Vitro Degradation of Natural Insoluble Lignin in Aqueous Media by the Extracellular Peroxidases of *Phanerochaete chrysosporium*," 1998 John Wiley & Sons, Inc. pp. 704-717.
Thompson et al., "Measurement of fumonsins in corn with a fiber-optic fluoroimmunosensor," SPIE vol. 2980, (2010) pp. 532-538.
Thompson et al., "Preliminary Investigation of Fungal Bioprocessing of Wheat Straw for Production of Straw-Thermoplastic Composites," Applied Biochemistry and Biotechnology, vol. 105-108, 2003, pp. 423-436.
Thompson et al., "Purification and Characterization of a Novel Thermo-Alkali-Stable Catalase from *Thermus brockianus*," Biotechnol. Prog. 2003, 19, 1292-1299.
Thompson et al., "Thermoacidophilic Cellulases and Hemicellulases from *Alicyclobacillus acidocaldarius*," Idaho National Laboratory, 2006, 1 page.
Thompson, et al., "Chapter 31: Changes in the Rate of Enzymatic Hydrolysis and Surface Area Available to Cellulase with Pretreatment Methods," Biotechnology in Pulp and Paper Manufacture: Applications and Fundamental Investigations. Proceedings of the Fourth International Conference on Biotechnology in the Pulp and Paper Industry (ICBPPI), May 16-19, 1989,Raleigh, NC and Myrtle Beach, SC, USA. Kirk, T.K. and Chang, H.M. (eds.). Butterworth-Heinemann, Boston, 1990, pp. 329-338.
Tsao, G.T., "Bacterial Hydrolysis: A Review," Anaerobic Digestion and Carbohydrate Hydrolysis of Waste, Ferrero et al. (eds.), Elsevier Applied Science Publishers, London, 1984, pp. 83-99.

Tsao, GT, MR Ladisch, and HR Bungay, 1987. Biomass Refining, In Advanced Biochemical Engineering, Wiley Interscience, N.Y., 79-101.

Turner et al., "Potential and utilization of thermophiles and thermostable enzymes in biorefining," Microbial Cell Factories, Biomed Central, London, NL, vol. 6, No. 1, Mar. 15, 2007, p. 9.

Extended Supplementary European Search Report for EP 09 70 9191, dated Mar. 29, 2012, 6 pages.

Database UniProt [Online]. Feb. 10, 2009. XP-002674095. Database accession No. B7DM51, 1 page.

Extended Supplementary European Search Report for EP 09 75 5307, dated Apr. 18, 2012, 4 pages.

GenBank: AJ252161.1 *Alicyclobacillus acidocaldarius* maltose/maltodextrine transport gene region(malEFGR genese, cdaA gene and glcA gene), NCBI, Hulsmann, A. http://www.ncbi.nlm.nih.gov/nuccore/AJ252161 (Jan. 6, 2000).

Extended Supplementary European Search Report for EP 10 74 6882, dated Aug. 27, 2012, 9 pages.

\* cited by examiner

METHODS OF COMBINED BIOPROCESSING AND RELATED MICROORGANISMS, THERMOPHILIC AND/OR ACIDOPHILIC ENZYMES, AND NUCLEIC ACIDS ENCODING SAID ENZYMES

CROSS-REFERENCE TO RELATED APPLICATIONS

This application is a continuation-in-part of U.S. patent application Ser. No. 12/322,359, filed Jan. 29, 2009, now U.S. Pat. No. 7,858,353, issued Dec. 28, 2010, to Thompson et al., which claims the benefit of U.S. Provisional Patent Application Ser. No. 61/025,136 filed Jan. 31, 2008, for "THERMOPHILIC AND THERMOACIDOPHILIC BIOPOLYMER-DEGRADING GENES AND ENZYMES FROM *ALICYCLOBACILLUS ACIDOCALDARIUS* AND RELATED ORGANISMS, METHODS"; is a continuation-in-part of U.S. patent application Ser. No. 12/380,551, filed Feb. 26, 2009, which claims the benefit of U.S. Provisional Patent Application Ser. No. 61/032,339 filed Feb. 28, 2008, for "THERMOPHILIC AND THERMOACIDOPHILIC METABOLISM GENES AND ENZYMES FROM *ALICYCLOBACILLUS ACIDOCALDARIUS* AND RELATED ORGANISMS, METHODS"; is a continuation-in-part of U.S. patent application Ser. No. 12/380,450, filed Feb. 26, 2009, which claims the benefit of U.S. Provisional Patent Application Ser. No. 61/031,984 filed Feb. 27, 2008, for "THERMOPHILIC AND THERMOACIDOPHILIC GLYCOSYLATION GENES AND ENZYMES FROM *ALICYCLOBACILLUS ACIDOCALDARIUS* AND RELATED ORGANISMS, METHODS"; is a continuation-in-part of U.S. patent application Ser. No. 12/380,554, filed Feb. 26, 2009, now U.S. Pat. No. 7,960,534, issued Jun. 14, 2011, to Thompson et al., which claims the benefit of U.S. Provisional Patent Application Ser. No. 61/031,593 filed Feb. 26, 2008, for "THERMOPHILIC AND THERMOACIDOPHILIC SUGAR TRANSPORTING GENES AND ENZYMES FROM *ALICYCLOBACILLUS ACIDOCALDARIUS* AND RELATED ORGANISMS, METHODS"; is a continuation-in-part of U.S. patent application Ser. No. 12/380,008, filed Feb. 20, 2009, which claims the benefit of U.S. Provisional Patent Application Ser. No. 61/030,820 filed Feb. 22, 2008, for "TRANSCRIPTIONAL CONTROL IN *ALICYCLOBACILLUS ACIDOCALDARIUS* AND ASSOCIATED GENES PROTEINS AND METHODS"; and is a continuation-in-part of U.S. patent application Ser. No. 12/321,636, filed Jan. 23, 2009, now U.S. Pat. No. 7,923,234, issued Apr. 12, 2011, to Thompson et al., which claims the benefit of U.S. Provisional Patent Application Ser. No. 61/023,639 filed Jan. 25, 2008 for "THERMAL AND ACID TOLERANT BETA-XYLOSIDASES, GENES ENCODING, RELATED ORGANISMS, AND METHODS."

GOVERNMENT RIGHTS

This invention was made with government support under Contract Number DE-AC07-99ID13727 and Contract Number DE-AC07-05ID14517 awarded by the United States Department of Energy. The government has certain rights in the invention.

STATEMENT ACCORDING TO 37 C.F.R. §1.52(e)(5)

Sequence Listing Submitted on Compact Disc

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "COPY 1 REPLACEMENT 01/18/2010" and "COPY 2 REPLACEMENT 01/18/2010," respectively, and each disc contains one file entitled "SEQ LIST II .ST25.txt," which is 1,837 KB and was created on Jan. 18, 2010.

BACKGROUND OF THE INVENTION

Dilute acid hydrolysis to remove hemicellulose from lignocellulosic materials is one of the most developed pretreatment techniques for lignocellulose and is currently favored (Hamelinck et al., 2005) because it results in fairly high yields of xylose (75% to 90%). Conditions that are typically used range from 0.1 to 1.5% sulfuric acid and temperatures above 160° C. The high temperatures used result in significant levels of thermal decomposition products that inhibit subsequent microbial fermentations (Lavarack et al., 2002). High temperature hydrolysis requires pressurized systems, steam generation, and corrosion resistant materials in reactor construction due to the more corrosive nature of acid at elevated temperatures.

Lower temperature acid hydrolyses are of interest because they have the potential to overcome several of the above shortcomings (Tsao et al., 1987). It has been demonstrated that 90% of hemicellulose can be solubilized as oligomers in a few hours of acid treatment in the temperature range of 80° C. to 100° C. It has also been demonstrated that the sugars produced in low temperature acid hydrolysis are stable under those same conditions for at least 24 hours with no detectable degradation to furfural decomposition products. Finally, sulfuric acid typically used in pretreatments is not as corrosive at lower temperatures. The use of lower temperature acid pretreatments requires much longer reaction times to achieve acceptable levels of hydrolysis. Although 90% hemicellulose solubilization has been shown (Tsao, 1987), the bulk of the sugars are in the form of oligomers and are not in the monomeric form. The organisms currently favored in subsequent fermentation steps cannot utilize sugar oligomers (Garrote et al., 2001) and the oligomer-containing hydrolysates require further processing to monomers, usually as a second acid or alkaline hydrolysis step (Garrote et al., 2001).

Other acidic pretreatment methods include autohydrolysis and hot water washing. In autohydrolysis, biomass is treated with steam at high temperatures (~240° C.), which cleaves acetyl side chains associated with hemicellulose to produce acetic acid that functions in a similar manner to sulfuric acid in acid hydrolysis. Higher pretreatment temperatures are required as compared to dilute sulfuric acid hydrolysis because acetic acid is a much weaker acid than sulfuric. At temperatures below 240° C., the hemicellulose is not completely hydrolyzed to sugar monomers and has high levels of oligomers (Garrote et al., 2001). In hot water washing, biomass is contacted with water (under pressure) at elevated temperatures 160° C. to 220° C. This process can effectively hydrolyze greater than 90% of the hemicellulose present, and the solubilized hemicellulose was typically over 95% in the form of oligomers (Liu and Wyman, 2003).

BRIEF SUMMARY OF THE INVENTION

The entire contents of each of the following applications are incorporated herein in their entirety by this reference: patent application Ser. Nos. 12/322,359 (filed Jan. 29, 2009); 12/321,636 (filed Jan. 23, 2009); 12/380,008 (filed Feb. 20, 2009); 12/380,554 (filed Feb. 26, 2009); 12/380,450 (filed Feb. 26, 2009); and 12/380,551 (filed Feb. 26, 2009).

Embodiments of the invention relate to a genetically modified organism for converting biomass into products. The genetically modified organism may comprise at least one nucleic acid sequence encoding a polypeptide as disclosed in the Patent Applications previously incorporated by reference herein. In embodiments, the genetically modified organism may comprise at least one nucleic acid sequence encoding a polypeptide associated with at least partially degrading, cleaving, transporting, metabolizing and/or removing polysaccharides, cellulose, hemicellulose, lignin, starch, sugars, sugar oligomers, carbohydrates, complex carbohydrates, chitin, heteroxylans, glycosides, xylan-, glucan-, galactan-, or mannan-decorating groups; and/or at least one nucleic acid sequence encoding a polypeptide associated with fermenting sugar molecules to products.

Embodiments of the invention also relate to protein(s) and/or cellular extracts isolated from a genetically modified organism. The isolated protein and/or cellular extracts may comprise: at least one polypeptide isolated from a genetically modified organism, the organism including: at least one recombinant nucleic acid encoding a polypeptide as disclosed in the Patent Applications previously incorporated by reference herein. In embodiments, the at least one recombinant nucleic acid encoding a polypeptide may comprise: at least one polypeptide involved in at least partially degrading, cleaving, transporting, metabolizing and/or removing polysaccharides, cellulose, hemicellulose, lignin, starch, sugars, sugar oligomers, carbohydrates, complex carbohydrates, chitin, heteroxylans, glycosides, xylan-, glucan-, galactan-, or mannan-decorating groups; and/or at least one recombinant nucleic acid encoding a polypeptide involved in fermenting sugar molecules to products.

Additional embodiments of the invention relate to methods of at least partially processing polysaccharides, cellulose, hemicellulose, starch, sugars, sugar oligomers, carbohydrates, complex carbohydrates, chitin, heteroxylans, glycosides, xylan-, glucan-, galactan-, or mannan-decorating groups into a product. The method may comprise: placing a genetically modified organism in fluid contact with a polysaccharide, cellulose, hemicellulose, starch, sugars, sugar oligomers, carbohydrates, complex carbohydrates, chitin, heteroxylans, glycoside, xylan-, glucan-, galactan-, and/or mannan-decorating group. The genetically modified organism may comprise at least one nucleic acid and/or at least one recombinant nucleic acid encoding a polypeptide involved in at least partially degrading, cleaving, transporting, metabolizing, or removing polysaccharides, cellulose, hemicellulose, lignin, starch, sugars, sugar oligomers, carbohydrates, complex carbohydrates, chitin, heteroxylans, glycosides, xylan-, glucan-, galactan-, or mannan-decorating groups; and/or at least one nucleic acid and/or at least one recombinant nucleic acid encoding a functional protein involved in fermenting sugar molecules to a product and/or a fermentation enzyme involved in converting sugars into a product.

Further embodiments of the invention relate to isolating an extract from a genetically modified organism according to the present invention. Embodiments may also include placing the isolated extract in fluid contact with a polysaccharide, cellulose, hemicellulose, lignin, starch, sugars, sugar oligomers, carbohydrates, complex carbohydrates, chitin, heteroxylans, glycoside, xylan-, glucan-, galactan-, and/or mannan-decorating group. The genetically modified organism may comprise at least one nucleic acid and/or at least one recombinant nucleic acid encoding a polypeptide having some level of activity in at least partially degrading, cleaving, transporting, metabolizing, and/or removing polysaccharides, cellulose, hemicellulose, lignin, starch, sugars, sugar oligomers, carbohydrates, complex carbohydrates, chitin, heteroxylans, glycosides, xylan-, glucan-, galactan-, or mannan-decorating groups; and/or at least one nucleic acid and/or at least one recombinant nucleic acid encoding a functional protein involved in fermenting sugar molecules to a product such as a fermentation or other enzyme involved in converting sugars into a product.

DETAILED DESCRIPTION OF THE INVENTION

Lignocellulose is a highly heterogeneous three-dimensional matrix comprised of cellulose, hemicellulose, and lignin. Many fuels and chemicals can be made from these lignocellulosic materials. To utilize lignocellulosic biomass for production of fuels and chemicals via fermentative processes, it is necessary to convert the plant polysaccharides to simpler sugars, which are then fermented to products using a variety of organisms. Direct hydrolysis of cellulose by mineral acids to monomers is possible at high temperature and pressure, leading to yield losses due to thermal decomposition of the sugars. One strategy to reduce these yield losses is to use cellulases and potentially other enzymes to depolymerize the polysaccharides at moderate temperatures. Addition of acid-stable thermotolerant hydrolytic enzymes such as cellulases and xylanases to the biomass slurry during the pretreatment allows the use of lower temperatures and pressures, as well as cheaper materials of reactor construction, reducing both the capital and energy costs. Another approach is to combine the reduced severity pretreatment with enzymes together with fermentation under the same conditions, using a single organism that produces the enzymes to degrade the material as well as ferment the sugars to the value-added product of choice.

For commercially available enzymes to be used for this purpose, the pretreatment slurry must be neutralized and cooled to 40° C. to 50° C., adding significant cost to the process. Hence, it would be an improvement in the art to degrade the soluble oligomers produced using acid, autohydrolysis or hot water washing pretreatments, at reduced severity and without neutralization using, for example, thermophilic and/or acidophilic enzymes.

Embodiments of the invention relate to a genetically modified organism comprising at least one of a nucleic acid sequence and protein sequence encoded by a nucleic acid sequence from *Alicyclobacillus acidocaldarius*. Such nucleic acids may include any of those nucleotide sequences described in the Patent Applications incorporated herein by reference. Such nucleic acids include, but are not limited to, those coding for enzymes capable of depolymerizing cellulosic polysaccharides to simpler carbohydrates and their transport into the bacterial cell and metabolism within the cell. Enzyme activities associated with transport into the cell and metabolism within the cell may be thermophilic and/or acidophilic in nature and general examples of nucleic acids coding for similar enzymes are described in the literature. Enzyme activities associated with cellulose depolymerization and/or metabolism may be thermophilic (intracellular) and/or thermoacidophilic (extracellular) and include, without limitation, the following classes of enzymes: Alpha-glucosidases, Glucan 1,4-alpha-maltohydrolases, Glycosidases, Amylases, Acetyl esterases, Beta-galactosidases, Alpha amylases, Alpha-xylosidases, Cyclomaltodextrinases; Neopullulanases; Maltogenic alpha-amylases, Family 31 of glycosyl hydrolase, Alpha-L-arabinofuranosidases, Altronate hydrolases, poly-1,4-alpha-D-galacturonidase Xylan alpha-1,2-glucuronosidases, Cellulase/Endoglucanase, Polygalacturonases, Glycosyl hydrolases, Peptidoglycan hydrolases, N-acetylglucosaminidases, Endochitinases, Alpha-galactosidases, Endo-beta-1,4-mannanases, Cellobiose phosphorylases, Cyclic beta-1,2-glucan synthases, Glycogen debranching enzymes, Acetyl hydrolases, Beta-1,4-xylanases, Beta-glucosidases, 6-phospho-beta-glucosidases, Cinnamoyl ester hydrolases, Beta-glucuronidases, Xylan alpha-1,2-glucuronosidases, 3-hydroxyisobutyryl-CoA hydrolases, Beta-glucosidases, glycosidases, Chitooligosaccharide deacetylases, glycosyl hydrolases (or glycoside hydrolases); esterases including acetylxylan esterases and p-cumaric acid esterases and ferulic acid esterases; and/or uronidases.

Additionally, embodiments of the invention relate in part to a genetically modified organism comprising, in addition to at least one of the nucleic acid sequences and protein sequences encoded by nucleic acids of *Alicyclobacillus acidocaldarius*, at least one of the nucleic acid sequences and protein sequences associated with fermenting sugar molecules to products. Such nucleic acid sequences may code for protein sequences which may be thermophilic and/or acidophilic in nature and general examples of similar nucleic acids are described in the literature.

The present invention also relates to isolated and/or purified nucleotide sequences from the genome of *Alicyclobacillus acidocaldarius* selected from the sequences described in the Patent Applications previously incorporated herein by reference.

Nucleotide, polynucleotide, or nucleic acid sequence will be understood according to the present invention as meaning either double-stranded or single-stranded DNA and the transcription products of said DNAs.

As used herein, "fermentation" relates to the biological conversion of a sugar molecule into a product. As used herein, a "product" is any chemical that can be made, at least in part, through a biological process. Examples of products include, but are not limited to, ethanol, acetic acid, glyoxylic acid, oxalic acid, lactic acid, 3-hydroxypropionic acid, glycerol, 1,2-propanediol, 1,3-propanediol, propionic acid, acetone, fumaric acid, succinic acid, malic acid, butyric acid, 1-butanol, 2,3-butanediol, acetoin, aspartic acid, 1,2,-butanediol, itaconic acid, glutamic acid, citric acid, aconitic acid, cis-cis muconic acid, gluconic acid, kojic acid, amino acids, vitamins, alginate, cellulose, curdlan, chondroitin, cyanophycin, gellan, heparin, hyaluronic acid, poly-gamma-glutamic acid, poly-epsilon-lysine, polyhydroxyalkanoates, pullulan, scleroglucan, xanthan, indigo, and those chemicals set forth in the BREW report from the University of Utrect, (Patel, M. et al., (2006), "Medium and long-term opportunities and risks of the biotechnological production of bulk chemicals from renewable resources: The potential of white biotechnology." The BREW Project. Final Report prepared under the European Commission's GROWTH Programme (DG Research), (publica.fraunhofer.de/eprints/N-48834.pdf)), the entirety of the contents of which are incorporated herein by this reference.

Although the following sections related to Hydrolysis Associated Molecules (HAMs) and Fermentation Associated Molecules (FAMs), the techniques therein apply equally to all other nucleotide sequences isolated and/or purified from the genome of acidophilic and or thermophilic organisms, such as, without limitation, *Alicyclobacillus acidocaldarius* and those HAMs and FAMs described in the Patent Applications previously incorporated herein by reference.

Expression/Integration of Hydrolysis Associated Molecules

In embodiments of the invention, one or more Hydrolysis Associated Molecules (HAMs) may be incorporated and/or inserted into an organism that has the ability to ferment sugars to products. The HAMs may include regulatory factors and/or nucleic acids coding for proteins associated with, involved in, and/or assisting in the breakdown and/or hydrolysis of biomass (i.e., polysaccharides, cellulose, lignocellulose, hemicellulose, lignin, starch, sugars, sugar oligomers, carbohydrates, complex carbohydrates, chitin, heteroxylans, glycosides, xylan-, glucan-, galactan-, or mannan-decorating groups, etc.) into more simple sugar molecules and/or sugar monomers. A non-exhaustive list of these proteins and/or enzymes include: cellulases (i.e., endo- and/or exo-cellulases such as endo-beta-1,4-glucanase or exo-beta-1,4-glucanase); hemicellulases (i.e., exo- and/or endo-beta-1,4-xylanase); one or more beta-xylosidase enzymes; B-1,4-cellobiohydrolases (CBH I & CBH II); xylanases (XYN I & XYN II); β-glucosidase; α-L-arabinofuranosidase; acetyl xylan esterase; β-mannanase; and α-glucuronidase; esterases of the alpha-beta hydrolase superfamily; alpha-beta hydrolase; alpha-glucosidases; alpha-xylosidase; alpha-L-arabinofuranosidase; altronate hydrolase; a cellulose/endoglucanase; a polygalacturonase; an alpha-galactosidase; a cellobiose phosphorylase; a glycogen debranching enzyme; an acetyl esterase/acetyl hydrolase; a beta-1,4-xylanase; a cinnamoyl ester hydrolase; a carboxylesterase type B; a beta-galactosidase/beta-glucuronidase; a xylan alpha-1,2-glucuronidase; a 3-hydroxyisobutyryl-CoA hydrolase; a beta-glucosidase B-related glycosidase; and/or a chitooligosaccharide deacetylase and/or so forth. Additional proteins and/or enzymes may include ligninolytic enzymes such as manganese peroxidase, lignin peroxidase, or the like.

Additionally, in embodiments, the HAMs may encompass all those nucleic acids and/or proteins associated with the replication, transcription, translation, and/or expression of nucleic acids involved with the breakdown and/or hydrolysis of biomass and/or lignocellulose into more simple sugar molecules and/or sugar monomers. In a non-limiting example, HAMs may comprise those nucleic acids involved with the regulation of hydrolysis, such as, but not limited to, those nucleic acids and/or proteins that increase the replication, transcription, expression, etc. of HAMs. Further, HAMs may comprise those nucleic acids and/or proteins that are involved with the down-regulation of other HAMs. A non-exhaustive list of these regulatory HAMs may include: transcription factors, enhancers, repressors, DNA binding proteins, or the like.

In embodiments, the HAMs may include derivatives, analogs, and/or modified versions of one or more HAMs. These derivative, analogs, and/or modified versions may include those modifications carried out in vivo or in vitro. Some non-limiting examples of derivative, analogs, and/or modifications include: substitutions, deletions, mutations, modifications etc. Modifications may comprise all modifications occurring to nucleic acids, DNA, RNA, proteins etc., such as, but not limited to, acetylation, deacetylation, alkylation, methylation, demethylation, carboxylation, glycosylation, phosphorylation, hydroxylation, PEGylation, biotinylation, and/or any other type of modification known in the art.

In embodiments, the HAMs may encompass those nucleic acids, proteins, and/or enzymes that are derivatives of HAMs and include tags, markers, and/or other modifications. A non-exhaustive list of tags may include: His-tags, FLAG tags, Calmodulin-tags, HA-tags, Maltose binding protein-tags, Thioredoxin-tags, S-tags, Strep-tags, Nus-tags, or the like. The HAMs may also includes those nucleic acids, proteins, and/or enzymes that include fluorescent markers, such as but not limited to, GFP, RFP, YFP, BFP, or the like.

In additional embodiments, HAMs may encompass nucleic acid or peptide signals that direct secretion of HAM proteins from the cell in which they are produced. Examples of such signals include N-terminal and/or C-terminal sequences that direct localization and/or secretion of the molecules with which they are associated. In further embodiments, HAMs may include transporter proteins, such as, by way of non-limiting example, ABC transporter proteins that direct the secretion of particular molecules (such as other HAMs) to the extracellular or periplasmic space. In embodiments, the signals may direct secretion of a HAM through any system for secretion including, but not limited to, Endoplasmic Reticulum/Golgi Apparatus systems; vesicle mediated secretion systems; any of the Type I, II, III, IV, V, VI, and/or Tat secretion systems; and/or Sec pathway systems.

The incorporation of the HAMs into the one or more organisms with the ability to ferment sugars to products may enable the one or more organisms to convert cellulosic and/or other biomass compositions into products in a variety of pH and temperature conditions. In one embodiment, the one or more genetically modified organisms may carry out the biomass conversion in a range of pH conditions from at or less than a pH of about 7; at or less than a pH of about 5, about a pH of 1 to about a pH of 5; and/or from about a pH of 1 to about a pH of 1.3.

In embodiments, the ability of a genetically modified organism according to the present invention to function and/or convert biomass into products in pH conditions of 1 to 5, may eliminate the need to neutralize and/or increase the pH to a range of about 5 to 6.0 for enzymatic hydrolysis and/or fermentation after dilute acid pretreatment, which, using conventional methods, is necessary for the hydrolysis and fermentation of cellulose to products. Indeed, in conventional methods of dilute acid hydrolysis, the pretreatment hydrolysate needs to be neutralized to enable enzymatic hydrolysis and fermentation to occur. As such, in one embodiment, the HAMs may code for thermophilic, thermoacidophilic, and/or acidophilic enzymes, properties and/or characteristics, or in the alternative they may be derived from one or more thermophilic, thermoacidophilic, and/or acidophilic organisms.

It is additionally contemplated that one or more of the HAM encoded proteins may function and/or have an optimum pH range of above a pH of 5. Indeed, one or more of the HAMs may function and/or enable breakdown and/or hydrolysis of biomass and/or cellulose into more simple sugar molecules and/or sugar monomers in pH conditions that range from a pH of about 5 to a pH of about 14.

In embodiments, one or more HAMs may function to and/or assist in the breakdown and/or hydrolysis of biomass and/or cellulosic materials into more simple sugar molecules and/or sugar monomers in a broad range of temperatures. Conventional methods and techniques of pretreatment for dilute acid hydrolysis and low temperature acid hydrolysis occur at temperature ranges of about 160 degrees Celsius and a range of eighty (80) degrees to one hundred (100) degrees Celsius, respectively. However, using the conventional methods, in order to begin the enzymatic hydrolysis and fermentation reactions, the pretreatment mixture/slurry needs to be cooled to around forty (40) degrees to fifty (50) degrees Celsius.

In contrast to the current and/or conventional methods, the HAMs incorporated into the organism may function to, assist in, and/or carry out the breakdown and/or hydrolysis of biomass and/or cellulosic materials into more simple sugar molecules and/or sugar monomers in a broad range of temperatures. Some non-limiting examples of temperature ranges include: at least about fifty (50) degrees Celsius; at least about seventy (70) degrees Celsius; from about forty-five (45) degrees Celsius to about eighty (80) degrees Celsius; from about eighty (80) degrees Celsius to about one hundred (100) degrees Celsius; from about eighty-five (85) degrees to about ninety-five (95) degrees Celsius; and/or from about ninety (90) degrees to about one hundred (100) degrees Celsius.

In embodiments, the one or more HAMs may be isolated from, derived from and/or originate from one or more organisms. The one or more organisms may comprise the same organism, organisms within the same genus and/or within the same species, and/or different and/or distinct organisms. In one non-limiting example, the HAMs are from one or more extremophiles, such as, but not limited to: hyperthermophilic, thermophilic, acidophilic, thermoacidophilic, and/or polyextremophilic organisms. Some non-limiting examples of organisms include: *Alicyclobacillus acisocaldarius; Clostridium thermocellum; Clostridium thermolacticum; Clostridium thermohydrosulfuricum; Trichoderma reesei*; a variety of *Bacillus* species (i.e., *B. subtilis, B. thermoamylovorans, B. stearothermophilus, B. granulobacter, B. pectinovorum, B. halodurans*, etc.); *Moorella thermoautotrophica; Moorella thermoacetica; Streptococcus (Lactobacillus) thermophilus*; and/or other extremophilic bacteria that possess one or more nucleic acids associated with the breakdown and/or hydrolysis of biomass and/or lignocellulosic material into more simple sugar molecules and/or sugar monomers. It is also contemplated that the HAMs may be isolated from, derived from, or otherwise originate from any type and/or kind of organism that includes one or more of the HAMs and/or other extremophilic bacteria that possess one or more nucleic acids encoding proteins involved in breakdown and/or hydrolysis of biomass and/or lignocellulosic material into products. It is also contemplated that the HAMs may be isolated from, derived from, or otherwise originate from any type and/or kind of organism that includes one or more of the HAMs, such as, but not limited to, those found online at wzw.tum.de/mbiotec/cellmo.htm; or available from an institution, such as, but not limited to, the Advanced Biotechnology Center (ABC) (Italy); Interlab Cell Line Collection (Biotechnology Dept.) (Italy); the Australian Government Analytical Laboratories (AGAL); the American Type Culture Collection (ATCC); the Belgian Coordinated Collections of Microorganisms (BCCM); the Prime Minister's Services Federal Office for Scientific, Technical and Cultural Affairs (OSTC) (Belgium); Bureau of Microbiology at Health Canada (BMHC); Centraalbureau voor Schimmelcultures (CBS) (the Netherlands); China Center for Type Culture Collection (CCTCC) (Wuhan); China Committee for Culture Collection of Microorganisms (Beijing); Colección Española de Cultivos Tipo (CECT) (Spain); Collection Nationale De Cultures De Microorganismes (CNCM) (Institut Pasteur, France); Collection of Industrial Yeasts DBVPG (Perugia, Italy); Culture Collection of Algae and Protozoa (CCAP) (United Kingdom); Culture Collection of Yeasts (CCY) (Slovakia); Czech Collection of Microorganisms (CCM); Deutsche Sammlung von Mikroorganismen and Zellkulturen GmbH (DSMZ) (Germany); European Collection of Cell Cultures (ECACC) (United Kingdom); Institute of Agriculture and Food Biotechnology (IAFB) Collection of Industrial Microorganisms (Poland); International Mycological Institute (IMI) (United Kingdom); International Patent Organism Depositary (IPOD) (Tsukuba, Japan); Korean Cell Line Research Foundation (KCLRF); Korean Collection for Type Cultures (KCTC); Korean Culture Center of Microorganisms (KCCM); Microbial Strain Collection of Latvia (MSCL); National Bank for Industrial Microorganisms and Cell Cultures (NBIMCC) (Bulgaria); National Collection of Agricultural and Industrial Microorganisms (NCAIM) (Budapest, Hungary); National Collection of Type Cultures (NCTC) (United Kingdom); National Collection of Yeast Cultures (NCYC); AFRC Institute of Food Research (United Kingdom); National Collections of Industrial, Food and Marine Bacteria (NCIMB) (Scotland); National Research Center of Antibiotics (Moscow); Polish Collection of Microorganisms (PCM) (Poland); Russian Collection of Microorganisms (VKM); and the Russian National Collection of Industrial Microorganisms (VKPM) (Russia).

In embodiments, one or more of the HAMs may be incorporated into, integrated into, and/or otherwise expressed in one or more organisms that may already have the ability to ferment sugars to products. Such organisms may be any organism known in the art that has the ability to ferment sugars to alcohols or other products. A non-exhaustive list of organisms may include: *Clostridium thermocellum*; *Clostridium thermolacticum*; *Clostridium thermohydrosulfuricum*; a variety of *Bacillus* species (i.e., *B. subtilis, B. thermoamylovorans, B. stearothermophilus, B. granulobacter, B. pectinovorum, B. halodurans*, etc.); *Moorella thermoautotrophica*; *Moorella thermoacetica*; *Streptococcus* (*Lactobacillus*) *thermophilus*; *Saccharomyces cerevisiae* (yeast), *Zymomonas mobilis, Candida shehatae, E. coli*, those found at any of the web sites or institutions listed herein, and/or other organisms that possess one or more nucleic acids coding for proteins involved in fermentation of sugars to products.

It is additionally contemplated that the organism able to ferment sugars to products may be any organism that has nucleic acids encoding for one or more proteins involved with the fermentation pathways, such as, but not limited to, hexokinase I, hexokinase II, glucokinase, glucose-6-phosphate isomerase, phosphofructokinase, aldolase, triosephosphate isomerase, glyceraldehyde-3-phosphate dehydrogenase, 3-phosphoglycerate kinase, phosphoglycerate mutase, enolase, enolase I, pyruvate decarboxylase, citrate synthase, aconitase, isocitrate dehydrogenase, succinate dehydrogenase, fumarase, xylose reductase, xylitol dehydrogenase, xylulokinase, phosphoketolase, lactate dehydrogenase, acetyl-CoA-acetyl transferase, β-hydroxybutyryl-CoA dehydrogenase, crotonase, butyryl CoA dehydrogenase, phosphobutyrylase, butyrate kinase, and alcohol dehydrogenase. In embodiments of the present invention, the organism may already include those enzymes and/or nucleic acids encoding enzymes, necessary for fermenting sugars to products. Some non-limiting examples of these enzymes include: hexokinase I, hexokinase II, glucokinase, glucose-6-phosphate isomerase, phosphofructokinase, aldolase, triosephosphate isomerase, glyceraldehyde-3-phosphate dehydrogenase, 3-phosphoglycerate kinase, phosphoglycerate mutase, enolase, enolase I, pyruvate decarboxylase, citrate synthase, aconitase, isocitrate dehydrogenase, succinate dehydrogenase, fumarase, xylose reductase, xylitol dehydrogenase, xylulokinase, phosphoketolase, lactate dehydrogenase, acetyl-CoA-acetyl transferase, β-hydroxybutyryl-CoA dehydrogenase, crotonse, butyryl CoA dehydrogenase, phosphobutyrylase, butyrate kinase, and alcohol dehydrogenase.

In embodiments, one or more of the HAMs may include and/or be expressed with one or more regulatory elements and/or proteins, such as, but not limited to, promoters, enhancers, transcription factors, activators, silencers, and/or so forth. Non-limiting examples of such regulatory elements may be found in the Patent Applications previously incorporated herein by reference. In this manner, the transcription and/or expression of one or more of the HAMs may be regulated and/or controlled. In a non-limiting example, the HAMs may include a promoter region substantially similar to promoter regions of one or more of the organism's Fermentation Associated Molecules (FAMs) (those nucleic acids encoding proteins involved in the fermentation of sugars to products). In this manner, transcription and/or expression of one or more of the HAMs occur at substantially the same time, or substantially simultaneous with, the transcription and/or expression of one or more of the FAMs. It is also contemplated that one or more of the HAMs may be included and/or integrated under the control of the same promoter and/or promoter regions of the FAMs in one or more of the organisms. Some non-limiting examples of types of promoters contemplated include: constitutive promoters, tissue specific or development stage promoters, inducible promoters, and/or synthetic promoters. In one embodiment, the promoter may be a standard promoter used in expression vectors, such as, but not limited to, the T7 and Sp6 Phage promoters, which promote the expression of inserted nucleic acids in a phage type vector.

In embodiments, one or more of the HAMs may comprise and/or be included in a delivery system that may deliver, incorporate, transfer, and/or assist in the delivery and/or expression of one or more of the HAMs into one or more of the organisms able to break down and/or convert cellulose to more simple sugar molecules. The delivery system may comprise any method for incorporating DNA, nucleic acids and/or vectors in cells known in the art, such as, but not limited to, transfection, electroporation, lipofection, transformation, gene guns, Biolistic Particle Delivery Systems, and/or so forth.

It is additionally contemplated that one or more HAMs may be incorporated into any type and/or kind of vector known in the art. A non-exhaustive list of potential vectors include: plasmids, bacteriophages, viruses, yeast artificial chromosomes (YACs) bacterial artificial chromosomes (BACs), P1 bacteriophage-derived chromosomes (PACs), mammalian artificial chromosomes, and/or so forth. The insertion and/or incorporation of desired nucleic acids into vectors is well understood, and in many instances vectors and/or insertion of nucleic acids into vectors are commercially available (i.e., through Empire genomics at empiregenomics.com/site/products_bacclones.php).

In embodiments, the delivery systems and/or vectors that may be used to incorporate one or more of the HAMs may include selective markers, tags, or the like. Such selective markers tags, etc., may enable the determination of a successful delivery, integration, and/or expression of a vector including one or more of the HAMs. Some non-limiting examples of selective markers, tags, etc., include: antibiotic resistance, amino acid/nutrient markers, color markers, fluorescent markers (i.e., GFP, RFP, etc.), His-tags, FLAG tags, Calmodulin-tags, HA-tags, Maltose binding protein-tags, Thioredoxin-tags, S-tags, Strep-tags, Nus-tags, and/or so forth.

In embodiments, it is contemplated that one or more of the HAMs may be integrated with, incorporated into, and/or become part of the genome and/or DNA of the host organism. Integrating one or more of the HAMs into the host DNA may provide for better expression, replication to subsequent host progeny, and/or protection from DNA degradation by the host organism. Numerous methods and/or vectors for integrating, inserting, and/or incorporating a desired nucleic acid into a host genome are well known in the art. A non-exhaustive list of potential vectors include: phage lambda (λ), adeno-associated virus (AAV), adenovirus, lentivirus, retroviruses, transposons, or the like. Additionally, a multipurpose vector system may be used as taught in Laitinen et al., A multipurpose vector system . . . , *Nucleic Acids Research* 2005, vol. 33, no. 4, which is incorporated by reference herein.

Expression/Integration of Fermentation Associated Molecules

In one embodiment of the invention one or more Fermentation Associated Molecules (FAMs), encoding for proteins associated with, involved in, and/or assisting in the fermentation of sugars to products may be incorporated and/or inserted into a organism that has the ability to break down lignocellulosic materials to more simple sugar molecules. The FAMs may include any nucleic acids, proteins and/or enzymes that are associated with the fermentation of sugars to products. A non-exhaustive list of these proteins and/or enzymes includes: hexokinase I, hexokinase II, glucokinase, glucose-6-phosphate isomerase, phosphofructokinase, aldolase, triosephosphate isomerase, glyceraldehyde-3-phosphate dehydrogenase, 3-phosphoglycerate kinase, phosphoglycerate mutase, enolase, enolase I, pyruvate decarboxylase, citrate synthase, aconitase, isocitrate dehydrogenase, succinate dehydrogenase, fumarase, xylose reductase, xylitol dehydrogenase, xylulokinase, phosphoketolase, lactate dehydrogenase, acetyl-CoA-acetyl transferase, β-hydroxybutyryl-CoA dehydrogenase, crotonase, butyryl CoA dehydrogenase, phosphobutyrylase, butyrate kinase, and alcohol dehydrogenase.

In additional embodiments, the FAMs encompass all those nucleic acids coding for proteins associated with the replication, transcription, translation, and/or expression of nucleic acids associated with the fermentation of sugars to a product. In a non-limiting example, FAMs may comprise those nucleic acids constituting either regulatory sequences or coding for proteins involved with the regulation of FAMs, such as, but not limited to, those nucleic acid sequences and/or proteins that increase replication, transcription, expression, etc., of FAMs. Further, FAMs may comprise those nucleic acids that are involved with the down-regulation of FAMs, either directly or through the proteins they may encode. A non-exhaustive list of proteins encoded by these FAMs may include: transcription factors, enhancers, repressors, DNA binding proteins, or the like.

In further embodiments, the FAMs may include derivatives, analogs, and/or modified versions of one or more FAMs. These derivatives, analogs, and/or modified versions may include those modifications carried out either in vivo or in vitro. Some non-limiting examples of derivatives, analogs, and/or modifications include: substitutions, deletions, mutations, modifications, etc. Modifications may comprise all modifications occurring to nucleic acids, DNA, RNA, proteins etc., such as, but not limited to, acetylation, deacetylation, alkylation, methylation, demethylation, carboxylation, glycosylation, phosphorylation, hydroxylation, PEGylation, biotinylation, and/or any other type of modification known in the art.

In yet other embodiments, the FAMs may encompass those nucleic acids, regulatory sequences, proteins, and/or enzymes which are encoded by the FAMs that are derivatives of FAMs and/or include tags, markers, and/or other modifications. A non-exhaustive list of tags may include: His-tags, FLAG tags, Calmodulin-tags, HA-tags, Maltose binding protein-tags, Thioredoxin-tags, S-tags, Strep-tags, Nus-tags, or the like. The FAMs may also includes those nucleic acids, proteins, and/or enzymes that include fluorescent markers, such as, but not limited to, GFP, RFP, YFP, BFP, or the like.

Advantageously, the incorporation of the FAMs into the one or more organisms with the ability to break down biomass to more simple sugar molecules may enable the one or more genetically modified organisms to convert lignocellulose and/or other biomass materials more efficiently into a product under a variety of pH and/or temperature conditions. In one embodiment, the one or more genetically modified organisms may carry out the biomass conversion in a range of pH conditions from at or less than a pH of about 7; at or less than a pH of about 5, from about a pH of 1 to about a pH of 5, and/or from about a pH of 1 to about a pH of 1.3.

Advantageously, in one embodiment, the ability of the genetically modified organism to function and/or convert biomass into products at pH conditions of 1 to 5, eliminates the need to neutralize and/or increase the pH to a range of about 5 to 6.0 for enzymatic hydrolysis and fermentation, which, using conventional methods, is necessary for the hydrolysis and fermentation of cellulose to products. Indeed, in conventional methods of dilute acid hydrolysis, the pretreatment hydrolysate needs to be neutralized to enable enzymatic hydrolysis and fermentation to occur. As such, in one embodiment, the FAMs may code for enzymes which comprise thermophilic, thermoacidophilic, and/or acidophilic properties and/or characteristics, or in the alternative may be derived from, analogs of, and/or homologues of one or more thermophilic, thermoacidophilic, and/or acidophilic FAMs from other organisms.

It is additionally contemplated that one or more of the proteins encoded by the FAMs may function and/or have an optimum pH range of above a pH of 5. Indeed, one or more of the proteins encoded by the FAMs may function and/or enable fermentation of sugar to products in pH conditions that range from a pH of about 5 to a pH of about 14.

In still another embodiment, enzymes encoded by one or more FAMs may function to and/or assist in fermenting sugars to products in a broad range of temperatures. Conventional methods and techniques of pretreatment using dilute acid hydrolysis and low temperature acid hydrolysis occur at temperature ranges of about 160 degrees Celsius and a range of eighty (80) degrees to one hundred (100) degrees Celsius, respectively. However, using the conventional methods, in order to begin the enzymatic hydrolysis and fermentation reactions, the pretreatment mixture/slurry needs to be cooled to around forty (40) degrees to fifty (50) degrees Celsius.

In contrast to the current and/or conventional methods, the FAMs incorporated into one or more of the organisms described herein may function to, assist in, and/or carry out the fermentation process in a broad range of temperatures. Some non-limiting examples of temperature ranges include: at least about fifty (50) degrees Celsius, at least about seventy (70) degrees Celsius, from about forty-five (45) degrees Celsius to about eighty (80) degrees Celsius; from about eighty (80) degrees Celsius to about one hundred (100) degrees Celsius; from about eighty-five (85) degrees to about ninety-five (95) degrees Celsius; and/or from about ninety (90) degrees to about one hundred (100) degrees Celsius.

In further embodiments, the one or more FAMs may be isolated from, derived from and/or originate from one or more organisms. The one or more organisms may comprise the same organism, organisms within the same genus and/or within the same species, and/or different and/or distinct organisms. In one non-limiting example, the FAMs are from one or more extremophiles, such as, but not limited to: hyperthermophilic, thermophilic, acidophilic, thermoacidophilic, and/or polyextremophilic organisms. Some non-limiting examples of organisms include: *Alicyclobacillus acidocaldarius, Clostridium thermocellum; Clostridium thermolacticum; Clostridium thermohydrosulfuricum*; a variety of *Bacillus* species (i.e., *B. subtilis, B. thermoamylovorans, B. stearothermophilus, B. granulobacter B. pectinovorum, B. halodurans*, etc.); *Moorella thermoautotrophica; Moorella thermoacetica; Streptococcus* (*Lactobacillus*) *thermophilus*, those found at any of the web sites or institutions listed herein, and/or other organisms that possess one or more nucleic acid sequences involved in fermentation of sugars to products. It is also contemplated that the FAMs may be isolated from, derived from, or otherwise originate from non-extremophilic organisms, such as, but not limited to, *Saccharomyces cerevisiae* (yeast), *Zymomonas mobilis, Candida shehatae, E. coli*, and/or other organisms which possess one or more nucleic acids involved in fermentation of sugars to products.

In embodiments, one or more of the FAMs may be incorporated into, integrated into, and/or otherwise expressed in one or more organisms that already have the ability to break down lignocellulose and/or biomass to more simple sugar molecules. Such organisms may be any organism known in the art that has the ability to break down lignocellulose to more simple sugar molecules. A non-exhaustive list of such organisms may include: *Alicyclobacillus acidocaldarius; Clostridium thermocellum; Clostridium thermohydrosulfuricum*; and/or any other organism that is known to have the ability to break down lignocellulose and/or biomass. It is additionally contemplated that the organism able to break down lignocellulose and/or biomass may be any organism that has nucleic acid sequences encoding one or more types of endo- and/or exo-cellulases, i.e., endo-beta-1,4-glucanase; one or more types of hemicellulases, i.e., endo-beta-1,4-xylanase; and/or one or more xylosidase enzymes.

In one embodiment of the present invention, an organism may already include enzymes and/or nucleic acids encoding enzymes, for breaking down at least one of the three major components of lignocellulose: cellulose, hemicellulose, and lignin. Some non-limiting examples of these enzymes include endo- and/or exo-β-1,4-glucanases. The endo- and/or exo-β-1,4-glucanases may function to hydrolyze the linked glucose residues (endo activity) and/or hydrolyze the ends of the cellulose polymers (exo activity). Additionally, the organism may already include endo-β-1,4-xylanase; and/or one or more xylosidase enzymes, such enzymes possessing the ability to hydrolyze one or more types of hemicellulose polymers. In an additional embodiment, the organism may include additional and/or accessory enzymes, proteins, or nucleic acid sequences that may assist in completely hydrolyzing, transporting, metabolizing and/or breaking down the one or more types of lignocellulose polymers into more simple sugar molecules and/or sugar monomers.

In embodiments, it is contemplated that the organism may include one or more enzymes and/or nucleic acids encoding enzymes that have the ability to break down, transport, metabolize, and/or hydrolyze lignin molecules; including nucleic acids encoding for ligninolytic enzymes such as manganese peroxidase, laccase, lignin peroxidase, or the like.

In embodiments, one or more of the FAMs may include and/or be expressed with one or more regulatory factors, regulatory elements, and/or proteins, such as, but not limited to, promoters, enhancers, transcription factors, activators, silencers, and/or so forth. Non-limiting examples of such regulatory elements may be found in the Patent Applications previously incorporated herein by reference. In this manner, the transcription and/or expression of one or more of the FAMs may be regulated and/or controlled. In a non-limiting example, the FAMs may include a promoter region substantially similar to promoter regions of one or more of the organism's Hydrolysis Associated Molecules (HAMs) (those nucleic acids involved in breaking down lignocellulosic materials to simpler sugars). In this manner, transcription and/or expression of one or more of the FAMs occur at substantially the same time, or substantially simultaneous with, the transcription and/or expression of the Hydrolysis Associated Molecules. It is also contemplated one or more of the FAMs may be included and/or integrated under the control of the same promoter and/or promoter regions of the Hydrolysis Associated Molecules in one or more of the organisms. Some non-limiting examples of types of promoters contemplated include: constitutive promoters, tissue specific or development stage promoters, inducible promoters, and/or synthetic promoters. In one embodiment, the promoter may be a standard promoter used in expression vectors, such as but not limited to, the T7 and Sp6 Phage promoters, which promote the expression of inserted nucleic acids in a phage type vector.

In embodiments, one or more of the FAMs may comprise and/or be included in a delivery system that may deliver, incorporate, transfer, and/or assist in the delivery and/or expression of one or more of the FAMs into one or more of the organisms able to break down and/or convert lignocellulose to more simple sugar molecules. The delivery system may comprise any method for incorporating DNA, nucleic acids and/or vectors into cells known in the art. A non-exhaustive list of methods may include: transfection, electroporation, lipofection, transformation, gene guns, Biolistic Particle Delivery System, and/or so forth.

It is additionally contemplated that one or more FAMs may be incorporated into any type and/or kind of vector known in the art. A non-exhaustive list of potential vectors include: plasmids, bacteriophages, viruses, yeast artificial chromosomes (YACs), bacterial artificial chromosomes (BACs), P1 bacteriophage-derived chromosomes (PACs), mammalian artificial chromosomes, and/or so forth. The insertion and/or incorporation of desired nucleic acids into vectors is well understood in the art, and in many instances vectors and/or insertion of nucleic acids into vectors are commercially available (i.e., through Empire genomics empiregenomics.com/site/products_bacclones.php).

In embodiments, the delivery systems and/or vectors that may be used to incorporate one or more of the FAMs may include and/or encode selective markers, tags, or the like, that may enable the determination of a successful delivery, integration, and/or expression of a vector including one or more of the FAMs. Some non-limiting examples of selective markers, tags, etc. include: antibiotic resistance, amino acid/nutrient markers, color markers, fluorescent markers (i.e., GFP, RFP, etc.), His-tags, FLAG tags, Calmodulin-tags, HA-tags, Maltose binding protein-tags, Thioredoxin-tags, S-tags, Strep-tags, Nus-tags, and so forth.

In embodiments, it is contemplated that one or more of the FAMs may be integrated with, incorporated into, and/or become part of the genome and/or DNA of the host organism. Integrating one or more of the FAMs into the host DNA may provide for better expression, replication to subsequent host progeny, and/or protection from DNA degradation by the host organism. There are numerous methods and/or vectors for integrating, inserting, and/or incorporating a desired nucleic acid into a host genome which are well known in the art. A non-exhaustive list of potential vectors include: phage lambda (λ), adeno-associated virus (AAV), adenovirus, lentivirus, retroviruses, transposons, or the like. Additionally, a multipurpose vector system may be used as taught in Laitinen et al., A multi-purpose vector system . . . , *Nucleic Acids Research*, 2005, vol. 33, no. 4, which is incorporated by reference herein.

BioProcessing

In embodiments, one of more of the genetically modified organisms described herein may produce one or more proteins from the FAMs and/or HAMs intracellularly and/or extracellularly. In producing proteins extracellularly, the genetically modified organism may excrete the proteins, enzymes, etc., into the extracellular and/or surrounding environment. It is additionally contemplated that the outer membrane and/or cell wall of the genetically modified organism may be coated with and/or include one or more proteins encoded by the HAMs. In this manner, breakdown and/or hydrolysis of biomass/lignocellulosic material is realized in the extracellular environment.

In embodiments, one or more of the genetically modified organisms described herein may convert biomass and/or lignocellulosic material to products at least partially intracellularly, or otherwise internal to the genetically modified organism. In a non-limiting example, at least partially hydrolyzed sugar molecules may be brought and/or transported into the genetically modified organism and fermented to ethanol or another product. The one or more genetically modified organism may then excrete the ethanol or other product into the extracellular environment.

It is contemplated that one more of the genetically modified organisms described herein may have multiple methods of use, uses, and/or applications in a wide variety of industries, laboratories, markets, etc.

In embodiments, one or more of the genetically modified organisms described herein may be applied to biomass and/or lignocellulosic material such that the biomass and/or lignocellulosic material is broken down, depolymerized, and subsequently converted to products. The one or more genetically modified organisms may be applied to the biomass or lignocellulosic material/composition in any manner known in the art. In a non-limiting example, the biomass and/or lignocellulosic material may be ground up and/or undergo a grinding process. Additionally, the biomass and/or lignocellulosic material may undergo various pretreatments prior to exposure to the recombinant organism. Such treatments may include, but are not limited to, sulfur dioxide, steam explosion, acid hydrolysis, ammonia hydrolysis, autohydrolysis, or the like. Additional, non-limiting examples are described in Thomas et al., which is incorporated by reference herein.

In embodiments, one or more of the genetically modified organisms described herein may be applied to biomass and/or lignocellulosic material, such as, but not limited to, cellulose, through the use of multiple methods and/or procedures. In one non-limiting example, a lignocellulosic composition may comprise one or more solid substrates/phases which are inoculated with the one or more genetically modified organisms, and/or cultures thereof. Additionally, the lignocellulosic composition may be embodied in a liquid, or substantially liquid substrate/phase; and the one or more genetically modified organisms introduced therein.

In embodiments, it is additionally contemplated that enzymes and/or proteins encoded by any and/or all of the HAMs and/or FAMs may be extracted, removed and/or isolated from one or more genetically modified organisms described herein. These enzymatic and/or proteinaceous compositions may then be applied to biomass and/or lignocellulosic material.

In embodiments, the biomass and/or lignocellulosic composition is inoculated with a genetically modified organism culture. It is contemplated there may be a variety of conditions (i.e., pH, concentrations of biomass and/or lignocellulosic material, concentration of genetically modified organisms, temperature, pressure, etc.) at which hydrolysis of the biomass and/or lignocellulosic material and subsequent fermentation may occur. Indeed, the pH of the hydrolysis may include ranges of at or less than a pH of about 7; at or less than a pH of about 5; about a pH of 1 to about a pH of 5; and/or from about a pH of 1 to about a pH of 1.3.

In embodiments, the ability of the one or more hydrolysis and/or fermentation reactions occurring in pH conditions of 1 to 5, may eliminate the need to neutralize and/or increase the pH to a range of about 5 to 6 following acid pretreatment for enzymatic hydrolysis and fermentation that, using conventional methods, is necessary for the hydrolysis and fermentation of lignocellulosic material to products. Indeed, in conventional methods of dilute acid hydrolysis, the pretreatment hydrolysate needs to be neutralized to enable enzymatic hydrolysis and fermentation to occur. As such, in one embodiment, the HAMs may code for enzymes that comprise thermophilic, thermoacidophilic, and/or acidophilic properties and/or characteristics, or in the alternative may be derived from one or more thermophilic, thermoacidophilic, and/or acidophilic organisms.

It is additionally contemplated that one or more hydrolysis and/or fermentation reactions may occur and/or have an optimum pH range of above a pH of 5. Indeed, the hydrolysis and/or fermentation reactions may occur in pH conditions that range from a pH of about 5 to a pH of about 14.

In embodiments, the one or more hydrolysis and/or fermentation reactions may occur in a broad range of temperatures. Some non-limiting examples of temperature ranges include: from about fifty (50) degrees Celsius; from about seventy (70) degrees Celsius; from about eighty (80) degrees Celsius to about one hundred (100) degrees Celsius; from about eighty-five (85) degrees to about ninety-five (95) degrees Celsius; and/or from about ninety (90) degrees to about one hundred (100) degrees Celsius.

In embodiments, one or more of the genetically modified organisms described herein may be grown and/or cultured in accordance with known methods. Such genetically modified organism cultures may be fluidly applied and/or contacted with biomass and/or lignocellulosic compositions, such as, but not limited to, polysaccharides, cellulose, lignocellulose, hemicellulose, lignin, starch, sugars, sugar oligomers, carbohydrates, complex carbohydrates, chitin, heteroxylans, glycosides, xylan-, glucan-, galactan-, or mannan-decorating groups.

In embodiments, cellular and/or proteinaceous extracts of the genetically modified organism cultures may be isolated. Protein and/or cellular isolations and extractions may be conducted through conventional methods. The cellular and/or proteinaceous extracts may be applied to and/or contacted with the biomass and/or lignocellulosic compositions as described herein.

In embodiments, one or more of the genetically modified organisms and/or one or more of the cellular and/or proteinaceous extracts described herein may be applied and/or fluidly contacted with biomass and/or lignocellulosic compositions under thermophilic, acidophilic, and/or thermoacidophilic conditions. In a non-limiting example, the temperature may be at or above about fifty (50) degrees and/or the pH at or below about the pH of 5 in a treatment mixture, slurry, apparatus or other area in which the fluid application occurs.

It is contemplated that a variety of conventional methods and/or techniques may be used to create the one or more genetically modified organisms described herein. One non-limiting method is described in U.S. Pat. No. 4,624,922, which is incorporated by reference herein.

Integration of Pretreatment, Biological Processing, and Product Recovery

Typically, the fermentative biological production of products from biomass proceeds through four distinct steps: pretreatment, cellulolytic hydrolysis, fermentation, and recovery. The pretreatment and recovery steps remain distinct in typical process designs, while the cellulolytic hydrolysis and fermentations steps can be separate steps or can be combined in various ways.

The pretreatment step is typically a physical or chemical pretreatment, such as an acid pretreatment, that effects a modification of the biomass to aid in further processing with cellulase enzymes. Typically, after a suitable period, the acid of the pretreatment is neutralized before initiating cellulolytic hydrolysis. In the most basic processing configuration, cellulolytic hydrolysis is carried out using exogenously added enzymes and is carried out separately from the fermentation step (separate hydrolysis and fermentation, or SHF). Glucose generated from the cellulose during cellulolytic hydrolysis, and pentose sugars released during the pretreatment, are separately consumed by fermenting organism(s) that are introduced to ferment the simple sugars into ethanol or another product of value. After fermentation, the product is recovered in a recovery step.

Additional processing configurations are typically utilized in which the cellulolytic hydrolysis using exogenously added enzymes and fermentation steps may be integrated. These include separate cellulolytic hydrolysis followed by co-fermentation of the pentose and hexose sugars (separate hydrolysis and co-fermentation, or SHCF), simultaneous cellulolytic hydrolysis and glucose fermentation (simultaneous saccharification and fermentation, or SSF) with separate pentose fermentation, simultaneous cellulolytic hydrolysis and co-fermentation of the glucose and pentose sugars (simultaneous saccharification and co-fermentation, or SSCF).

A final processing configuration can be used in which the organism utilized to ferment glucose released during cellulolytic hydrolysis serves as the source of the cellulolytic enzymes. In this configuration, a physical and/or chemical pretreatment is utilized to improve the action of the endogenously produced cellulolytic enzymes on the cellulose. This processing configuration is referred to as Consolidated Bioprocessing (CBP).

In embodiments of the invention, the above schemes may be modified through the use of enzymes and/or organisms active and stable at increased temperatures and decreased pH to allow the combination of pretreatment and/or product recovery with the conventional biological processing steps. In certain embodiments, the pretreatment may be conducted at lowered temperatures relative to existing dilute acid pretreatment technology and this step may be carried out enzymatically utilizing thermoacidophilic lignocellulose-degrading enzymes. The altered pretreatment and subsequent biological processing (cellulolytic hydrolysis and fermentation) may be carried out sequentially or combined together. The pretreatment and biological processing, may, in certain embodiments, be carried out by isolated enzymes and/or organisms for the cellulolytic hydrolysis and/or fermentation steps according to the present invention. The enzymes may be added exogenously or may be produced by the fermentation organisms in a Combined Pretreatment and Consolidated Bioprocessing (CPBP) configuration. In certain embodiments, the thermoacidophilic enzymes and organisms may include *Alicyclobacillus acidocaldarius*, genetically modified organisms comprising one or more nucleotides sequences derived or isolated from *Alicyclobacillus acidocaldarius*, or by extracts and/or lysates comprising one or more proteins produced by or derived from *Alicyclobacillus acidocaldarius*. In embodiments, the pretreatment step may comprise an acid pretreatment; alkaline pretreatment; hydrothermal pretreatment; and/or an organosolvent pretreatment.

In further embodiments, the acid or alkali added to or generated during a pretreatment step may not need to be neutralized before hydrolysis and/or fermentation. In embodiments, the non-neutralization of the pretreatment conditions may lead to the decreased function or death of any unwanted organisms present on the incoming biomass to be treated. In embodiments, the non-neutralization of the pretreatment conditions may result in decreased byproducts or unwanted products as the function of any unwanted organisms present on the incoming biomass to be treated may be decreased.

In additional embodiments, one or more genetically modified organisms, HAMs, and/or FAMs according to the present invention may play a role in the pretreatment, cellulolytic hydrolysis, and fermentation, or in any combination thereof. For example, a genetically modified organism according to the present invention may carry out processes contributing to pretreatment and cellulolytic hydrolysis, and a second genetically modified organism according to the present invention may separately or simultaneously carry out the fermentation. In another non-limiting example, thermoacidophilic enzymes according to the present invention may carry out processes contributing to pretreatment, and one or more genetically modified organism(s) according to the present invention may carry out processes contributing to cellulolytic hydrolysis and/or fermentation. In a further non-limiting example, a single genetically modified organism(s) according to the present invention may carry out processes contributing to pretreatment, cellulolytic hydrolysis, and fermentation.

In embodiments, a reduced severity acid pretreatment step may be combined with, or occur sequentially with, the addition of thermoacidophilic lignocellulose-degrading enzymes, and occur separately or concurrently with one or both of the cellulolytic hydrolysis and fermentation steps.

Expression/Integration of Hydrolysis Associated Molecules and Fermentation Associated Molecules In embodiments of the invention one or more Hydrolysis Associated Molecules (HAMs) and/or one or more Fermentation Associated Molecules (FAMs) may be incorporated and/or inserted into an organism.

The incorporation of the HAMs and FAMs into the one or more organisms may enable the one or more organisms to convert lignocellulosic and/or other biomass materials into a product at a variety of pH and temperature conditions. In one embodiment, the one or more genetically modified organisms may carry out the biomass conversion in a range of pH conditions from at or less than a pH of about 7; at or less than a pH of about 5; about a pH of 1 to about a pH of 5; and/or from about a pH of 1 to about a pH of 1.3.

In embodiments, the ability of the organism(s) to function and/or convert biomass into products in pH conditions of 1 to 5, may eliminate the need to neutralize and/or increase the pH to a range of about 5 to 6 for enzymatic hydrolysis and/or fermentation after dilute acid pretreatment, which, using conventional methods, is necessary for the hydrolysis and fermentation of cellulose to products. Indeed, in conventional methods of dilute acid hydrolysis, the pretreatment hydrolysate needs to be neutralized to enable enzymatic hydrolysis and fermentation to occur. As such, in one embodiment, the HAMs and FAMs may code for or be enzymes that possess thermophilic, thermoacidophilic, and/or acidophilic properties and/or characteristics, or in the alternative may be derived from one or more thermophilic, thermoacidophilic, and/or acidophilic organisms.

It is additionally contemplated that one or more of the HAMs and FAMs may function and/or have an optimum pH range of above a pH of 5. Indeed, one or more of the HAMs and FAMs may function and/or enable breakdown and/or hydrolysis of biomass and/or lignocellulosic material into products in pH conditions that range from a pH of about 5 to a pH of about 14.

Conventional methods and techniques of pretreatment for dilute acid hydrolysis and low temperature acid hydrolysis occur at temperature ranges of about 160 degrees Celsius and a range of eighty (80) degrees to one hundred (100) degrees Celsius, respectively. However, using the conventional methods, in order to begin the enzymatic hydrolysis and fermentation reactions, the pretreatment mixture/slurry needs to be cooled to around forty (40) degrees to fifty (50) degrees Celsius.

In contrast to the current and/or conventional methods, the HAMs and FAMs may function to, assist in, and/or carry out the breakdown and/or hydrolysis of biomass and/or lignocellulose into products in a broad range of temperatures. Some non-limiting examples of temperature ranges include: at least about fifty (50) degrees Celsius; at least about seventy (70) degrees Celsius; from about forty-five (45) degrees Celsius to about eighty (80) degrees Celsius; from about eighty (80) degrees Celsius to about one hundred (100) degrees Celsius; from about eighty-five (85) degrees to about ninety-five (95) degrees Celsius; and/or from about ninety (90) degrees to about one hundred (100) degrees Celsius).

In embodiments, the one or more HAMs and FAMs may be isolated from, derived from and/or originate from one or more organisms. The one or more organisms may comprise the same organism, organisms within the same genus and/or within the same species, and/or different and/or distinct organisms. In one non-limiting example, the HAMs and FAMs are from one or more extremophiles, such as, but not limited to: hyperthermophilic, thermophilic, acidophilic, thermoacidophilic, and/or polyextremophilic organisms. Some non-limiting examples of organisms include: *Alicyclobacillus acidocaldarius; Clostridium thermocellum; Clostridium thermolacticum; Clostridium thermohydrosulfuricum; Trichoderma reesei*; a variety of *Bacillus* species (i.e., *B. subtilis, B. thermoamylovorans, B. stearothermophilus, B. granulobacter B. pectinovorum, B. halodurans*, etc.); *Moorella thermoautotrophica; Moorella thermoacetica; Streptococcus (Lactobacillus) thermophilus*; and/or other extremophilic organisms that possess one or more nucleic acids encoding proteins involved in breakdown and/or hydrolysis of biomass and/or lignocellulosic material and fermentation of sugars into products. It is also contemplated that the HAMs and FAMs may be isolated from, derived from, or otherwise originate from any type and/or kind of organism that includes one or more of the HAMs and FAMs such as, but not limited to, those found at any of the web sites or institutions listed herein.

In embodiments, one or more of the HAMs and FAMs may be incorporated into, integrated into, and/or otherwise expressed in one or more organisms that do not have the ability to break down and/or hydrolyze biomass and/or lignocellulose and/or ferment sugars to products. Such organisms may be any organism known in the art, such as, but not limited to, *E. coli, Thermus thermophilus*, and/or any other suitable organism known in the art.

In embodiments, one or more of the HAMs and FAMs may include and/or be expressed with one or more regulatory elements and/or proteins, such as, but not limited to, promoters, enhancers, transcription factors, activators, silencers, and/or so forth. Non-limiting examples of such regulatory factors may be found in the Patent Applications previously incorporated herein by reference. In this manner, the transcription and/or expression of one or more of the HAMs and FAMs may be regulated and/or controlled. In a non-limiting example, the HAMs and FAMs may include a promoter region substantially similar to promoter regions of one or more of the organism's Fermentation Associated Molecules (those nucleic acids involved in the fermentation of sugars to products). In this manner, transcription and/or expression of one or more of the HAMs and FAMs occur at substantially the same time, or substantially simultaneous with, the transcription and/or expression of the endogenous FAMs.

It is also contemplated that one or more of the HAMs and FAMs may be included and/or integrated under the control of the same promoter and/or promoter regions in one or more of the organisms. Some non-limiting examples of types of promoters contemplated include: constitutive promoters, tissues specific or development stage promoters, inducible promoters, and/or synthetic promoters. In one embodiment, the promoter may be a standard promoter used in expression vectors, such as, but not limited to, the T7 and Sp6 Phage promoters, which promote the expression of inserted nucleic acids in a phage type vector.

In embodiments, one or more of the HAMs and FAMs may comprise and/or be included in a delivery system that may deliver, incorporate, transfer, and/or assist in the delivery and/or expression of one or more of the HAMs and FAMs into one or more organisms. The delivery system may comprise any method for incorporating DNA, nucleic acids and/or vectors in cells known in the art, such as, but not limited to, transfection, electroporation, lipofection, transformation, gene guns, Biolistic Particle Delivery Systems, and/or so forth.

It is additionally contemplated that one or more HAMs and FAMs may be incorporated into any type and/or kind of vector known in the art. A non-exhaustive list of potential vectors include: transposons, plasmids, bacteriophages, viruses, yeast artificial chromosomes (YACs), bacterial artificial chromosomes (BACs), P1 bacteriophage-derived chromosomes (PACs), mammalian artificial chromosomes, and/or so forth. The insertion and/or incorporation of desired nucleic acids into vectors is well understood in the art, and in many instances vectors and/or insertion of nucleic acids into vectors are commercially available (i.e., through Empire genomics at empiregenomics.com/site/products_bac-clones.php).

In embodiments, the delivery systems and/or vectors that may be used to incorporate one or more of the HAMs and FAMs may include selective markers, tags, or the like. Such selective marker and/or tags may enable the determination of successful delivery, integration, and/or expression of a vector including one or more of the HAMs and FAMs. Some non-limiting examples of selective markers, tags, etc., include: antibiotic resistance, amino acid/nutrient markers, color markers, fluorescent markers (i.e., GFP, RFP, etc.), His-tags, FLAG tags, Calmodulin-tags, HA-tags, Maltose binding protein-tags, Thioredoxin-tags, S-tags, Strep-tags, Nus-tags, and/or so forth.

In embodiments, it is contemplated that one or more of the HAMs and FAMs may be integrated with, incorporated into, and/or become part of the genome and/or DNA of the host organism. Integrating one or more of the HAMs and FAMs into the host DNA may provide for better expression, replication to subsequent host progeny, and/or protection from DNA degradation by the host organism. Numerous methods and/or vectors for integrating, inserting, and/or incorporating a desired nucleic acid into a host genome are well known in the art. A non-exhaustive list of potential vectors include: phage lambda (λ), adeno-associated virus (AAV), adenovirus, lentivirus, retroviruses, transposons, or the like. Additionally, a multipurpose vector system may be used as taught in Laitinen et al., 2005, A multi-purpose vector system . . . , *Nucleic Acids Research*, vol. 33, no. 4, which is incorporated by reference herein.

EXAMPLES

Example 1

Delivery/Expression of Fermentation Associated Molecules in *Alicyclobacillus acidocaldarius*

Nucleic acids encoding enzymes involved in the fermentation of sugars (i.e., glucose, xylose, galactose, arabinose, mannose, etc.) to products are provided to and subsequently expressed in *Alicyclobacillus acidocaldarius* u sing conventional molecular cloning techniques. Nucleic acids to be provided include those nucleic acids encoding for the proteins involved in the pathways that convert sugars to a product (FAMs). A non-exhaustive list of these proteins include: hexokinase I, hexokinase II, glucokinase, glucose-6-phosphate isomerase, phosphofructokinase, aldolase, triosephosphate isomerase, glyceraldehyde-3-phosphate dehydrogenase, 3-phosphoglycerate kinase, phosphoglycerate mutase, enolase, enolase I, pyruvate decarboxylase, citrate synthase, aconitase, isocitrate dehydrogenase, succinate dehydrogenase, fumarase, xylose reductase, xylitol dehydrogenase, xylulokinase, phosphoketolase, lactate dehydrogenase, acetyl-CoA-acetyl transferase, β-hydroxybutyryl-CoA dehydrogenase, crotonase, butyryl CoA dehydrogenase, phosphobutyrylase, butyrate kinase, and alcohol dehydrogenase. The FAMs may comprise nucleic acids from a wide variety of organisms that use fermentation pathways. Some non-limiting examples of these organisms include: *Saccharomyces cerevisiae* (yeast); *Clostridium thermocellum; Clostridium thermohydrosulfuricum*; a variety of *Bacillus* species (i.e., *B. subtilis, B. thermoamylovorans, B. stearothermophilus, B. granulobacter, B. pectinovorum, B. halodurans*, and/or so forth); *Alicyclobacillus acidocaldarius; Clostridium thermolacticum; Trichoderma reesei; Moorella thermoautotrophica; Moorella thermoacetica; Streptococcus (Lactobacillus) thermophilus*; and/or those found at any of the web sites or institutions listed herein.

Example 1(a)

Delivery of FAMs via a Transpososome

A transpososome is constructed to include nucleic acids encoding proteins involved in fermentation of sugars, or FAMs. Included in the transpososome are the nucleic acids necessary for insertion of the transposon, copies of the MuA transposase, Mu transposon ends, and provision for expression of the FAMs included in the transpososome in the particular organism in which they are to be utilized. Transpososomes may also be constructed using sequences and elements optimized for use in gram-positive bacteria. See, Pajunen et al., *Microbiology* (2005) 151, 1209-1218. Conventional techniques may be used to construct the transpososome. Additionally, the construction and/or insertion of desired nucleic acids into transpososomes is well known in the art, see, Pajunen et al. It is contemplated that multiple transpososomes may be constructed with FAMs and may include a variety of promoters, enhancers that may function to enhance and/or regulate expression of FAMs.

Once constructed, the transpososomes are introduced into *Alicyclobacillus acidocaldarius*. Transpososome constructs may be introduced into *A. acidocaldarius* by electroporation, and so forth. Such techniques are known in the art and are detailed in Sambrook J.C., R. Fritsch, and T. Maniatas, 1989. *Molecular Cloning: A Laboratory Manual*, 2nd ed., Cold Spring Harbor Laboratory Press, N.Y., pp. 6.3-6.34; or Sambrook and Russell, *Molecular Cloning: A Laboratory Manual (3-Volume Set)*, $3^{rd}$ ed. (available online at molecularcloning.com/); both references incorporated by reference herein.

Example 2

Delivery/Expression of Hydrolysis Associated Molecules into an Organism Able to Ferment Sugar to Ethanol Nucleic acids encoding enzymes involved in the hydrolysis, or breakdown, of lignocellulosic materials (i.e., biomass, cellulose, hemicellulose, etc.) to simpler sugars (Hydrolysis Associated Molecules (HAMs)) are genetically introduced by conventional molecular cloning techniques into organisms that ferment sugars to ethanol and subsequently expressed therein. HAMs to be provided include those nucleic acids coding for the proteins involved in the pathways that break down or hydrolyze cellulose, hemicellulose, etc., to more simple sugar molecules. A non-exhaustive list of these proteins include: esterases of the alpha-beta hydrolase superfamily; alpha beta hydrolase; alpha-glucosidases; alpha-xylosidase; alpha-L-arabinofuranosidase; altronate hydrolase; a cellulose/endoglucanase; a cellulase/endoglucanase; a polygalacturonase; an alpha-galactosidase; a cellobiose phosphorylase; a glycogen debranching enzyme; an acetyl esterase/acetyl hydrolase; a beta-1,4-xylanase; a cinnamoyl ester hydrolase; a carboxylesterase type B; a beta-galactosidase/beta-glucuronidase; a xylan alpha-1,2-glucuronidase; a 3-hydroxyisobutyryl-CoA hydrolase; a beta-glucosidase B-related glycosidase; and/or a chitooligosaccharide deacetylase, or as described herein. The HAMs may comprise nucleic acids from a wide variety of organisms that are able to hydrolyze and/or break down lignocellulosic material to more simple sugar molecules.

Example 2(a)

Delivery of HAMs Via a Transpososome

A transpososome is constructed to include nucleic acids encoding proteins involved in hydrolysis or breakdown of lignocellulosic polymers, or HAMs. Included in the transpososome are the nucleic acids necessary for insertion of the transposon, copies of the MuA transposase, Mu transposon ends, and provision for expression of the HAMs included in the transpososome in the particular organism in which they are to be utilized. Transpososomes may also be constructed using sequences and elements optimized for use in gram-positive bacteria. See, Pajunen et al., *Microbiology* (2005) 151, 1209-1218. Conventional techniques may be used to construct the transpososome. Additionally, the construction and/or insertion of desired nucleic acids into transpososomes is well known in the art, see, Pajunen et al. It is contemplated that multiple transpososomes may be constructed with HAMs and may include a variety of promoters, enhancers that may function to enhance and/or regulate expression of HAMs.

Once constructed, the transpososomes are introduced into an organism that is able to ferment and/or convert sugar molecules to a product. A non-exhaustive list of potential organisms include: *Clostridium thermocellum; Clostridium thermohydrosulfuricum*; a variety of *Bacillus* species (i.e., *B. subtilis, B. thermoamylovorans, B. stearothermophilus, B. granulobacter, B. pectinovorum, B. halodurans*, and/or so forth); and/or those described herein. The transpososome HAM constructs may be introduced into the organism by any technique known in the art, such as, but not limited to, electroporation, and so forth. Such techniques are known in the art and are detailed in Sambrook J.C., R. Fritsch, and T. Maniatas, 1989. *Molecular Cloning: A Laboratory Manual*, 2nd ed., Cold Spring Harbor Laboratory Press, N.Y, pp. 6.3-6.34; or Sambrook and Russell, Molecular Cloning: A Laboratory Manual (3-Volume Set), $3^{rd}$ ed. (available online at molecularcloning.com/); both references incorporated by reference herein.

Example 2(b)

Recombination/Integration of Hydrolysis Associated Molecules into Genome of Organism Able to Ferment Sugar to Ethanol One or more HAMs are integrated into the genome of an organism that is able to ferment and/or convert sugar molecules to a product. A transpososome is made that includes the HAMs and contains sequences for promoting the integration of the included HAM(s) into the genome. The transpososome construct may be any type and/or kind of transpososome construct known in the art, such that the transpososome construct assists in the integration of the one or more HAMs into a host genome. Such transpososome may include Mu based transpososomes or the like.

Example 3

Transformation/Expression of Hydrolysis Associated Molecules and Fermentation Associated Molecules in a Organism Both HAMs and FAMs are expressed in a suitable organism. The HAMs and FAMs to be expressed include any and/or all of the Hydrolysis or Fermentation Associated Molecules as described herein.

Example 3(a)

Transformation of Hydrolysis Associated Molecules and Fermentation Associated Molecules Using a Transpososome One or more transpososomes are constructed including HAMs and/or FAMs. Similar to Example 1 and Example 2, included in each of the transpososomes are the nucleic acids necessary for insertion and expression of the nucleic acids in the transpososome. Included in the transpososome are the nucleic acids necessary for insertion of the transposon, copies of the MuA transposase, Mu transposon ends, and provision for expression of the nucleic acids contained in the transpososome in the particular organism in which they are to be utilized. Transpososomes may also be constructed using sequences and elements optimized for use in gram-positive bacteria. See, Pajunen et al., *Microbiology* (2005) 151, 1209-1218. Conventional techniques may be used to construct the transpososome. Additionally, the construction and/or insertion of desired nucleic acids into transpososomes is well known in the art, see, Pajunen et al. It is contemplated that multiple transpososomes may be constructed with the HAMs and FAMs, and may include a variety of promoters and/or enhancers that may function to enhance expression of HAMs and/or FAMs.

Once constructed, the transpososomes are introduced into a target organism. Some non-limiting examples of potential organisms include *E. coli*, any type and/or kind of thermophilic bacteria (e.g., *Sulfolobus, Thermoproteus*, etc.), and/or so forth. The transpososome constructs may be introduced into the organism by any technique known in the art, or as described herein.

Example 3(b)

Integration of Hydrolysis and Fermentation Associated Molecules into Genome of Organisms One or more FAMs and/or HAMs are integrated into the genome of *A. acidocaldarius*. A transpososome is made that includes FAMs and/or HAMs and contains sequences for promoting the integration of the included FAMs and/or HAMs into the genome. The transpososome may be any type and/or kind of transpososome construct known in the art, such that the transpososome assists in the integration of the one or more FAMs and/or HAMs into a host genome. Such transpososomes may include Mu based transpososomes or the like.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims and their legal equivalents.

BIBLIOGRAPHIC REFERENCES

Garrote, G., H. Dominguez, and J.C. Parajo, 2001, Manufacture of xylose-based fermentation media from corncobs by posthydrolysis of autohydrolysis liquors, *Appl. Biochem. Biotechnol.*, 95:195-207.

Hamelinck, C.N., G. van Hooijdonk, and A.P.C. Faaij, 2005, Ethanol from lignocellulosic biomass: techno-economic performance in short-, middle-, and long-term, *Biomass Bioenergy*, 28:384-410.

Laitinen et al., 2005, A Multipurpose Vector system for the screening of libraries in bacteria, insect and mammalian cells and expression in vivo, *Nucleic Acids Research* 33(4)

Liu C., and C.E. Wyman, 2003, The effect of flow rate of compressed hot water on xylan, lignin, and total mass removal from corn stover, *Ind. Eng. Chem. Res.*, 42:5409-5416.

Lynd et al., 2002, *Micro. and Mol. Biol. Rev.*, Vol. 66, No. 3, pp. 506-577.

Sambrook J.C., R. Fritsch, Maniatas T., 1989. *Molecular Cloning: A Laboratory Manual*, 2nd ed., Cold Spring Harbor Laboratory Press, N.Y, pp. 6.3-6.34.

Sambrook and Russell, 2001, *Molecular Cloning: A Laboratory Manual (3-Volume Set)*, $3^{rd}$ ed. (available online at molecularcloning.com/).

Ng et al., 1981, *Applied and Environmental Microbiology*, 41(6):1337-1343.

Tsao, G.T., M.R. Ladisch, and H.R. Bungay, 1987. Biomass Refining, In *Advanced Biochemical Engineering*, Wiley Interscience, N.Y., pp. 79-101.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08492114B2). An electronic copy of the "Sequence Listing" will also be available from the USPTO upon request and payment of the fee set forth in 37 CFR 1.19(b)(3).

What is claimed is:

1. A genetically modified bacterial or fungal organism, the genetically modified organism comprising:
   at least one exogenous nucleic acid isolated from *Alicyclobacillus acidocaldarius* and encoding a polypeptide having at least 90% homology to SEQ ID NO:270 and wherein the polypeptide has beta-1,4-xylanase activity; and
   at least one nucleic acid sequence encoding a polypeptide associated with fermenting sugar molecules to a product.

2. The genetically modified organism of claim 1, wherein the at least one nucleic acid from *Alicyclobacillus acidocaldarius* is integrated into the host organism's genome.

3. The genetically modified organism of claim 1, wherein the polypeptide has beta-1,4-xylanase activity at or above about fifty degrees Celsius.

4. The genetically modified organism of claim 1, wherein the polypeptide comprises SEQ ID NO:270.

5. The genetically modified organism of claim 1, wherein the nucleic acid isolated from *Alicyclobacillus acidocaldarius* has at least 90% homology to SEQ ID NO:269.

6. The genetically modified organism of claim 1, wherein the nucleic acid isolated from *Alicyclobacillus acidocaldarius* is SEQ ID NO:269.

7. An extract isolated from the genetically modified organism of claim 1.

8. A method for at least partially processing hemicellulose into a product, the method comprising:
   contacting a liquid culture medium of the genetically modified organism of claim 1 with hemicellulose.

9. The method according to claim 8, wherein the contacting occurs at or above about fifty degrees Celsius.

10. A method for at least partially processing hemicellulose, the method comprising:
    isolating an enzyme extract from the genetically modified organism of claim 1; and
    contacting the extract with hemicellulose.

11. A method of producing a product from biomass, the method comprising:
    pretreating the biomass with an acid;
    enzymatically hydrolyzing cellulose and hemicellulose in the biomass to more simple sugars and concurrently fermenting the more simple sugars to a product; and
    recovering the product;
    wherein at least a portion of the hydrolyzing of cellulose and hemicellulose or the fermentation is performed by the genetically modified organism of claim 1.

12. A method of producing a product from biomass, the method comprising:
    treating the biomass with an acid;
    enzymatically hydrolyzing cellulose and hemicellulose in the biomass to more simple sugars;
    fermenting the more simple sugars to a product; and
    recovering the product;
    wherein at least a portion of the hydrolyzing of cellulose and hemicellulose or the fermentation is performed by the genetically modified organism according to claim 1; and
    wherein the pretreatment, the hydrolyzing of cellulose and hemicellulose, and the fermentation are performed concurrently.

13. A method of processing biomass, the method comprising:
    pretreating the biomass with an acid and concurrently enzymatically hydrolyzing cellulose and hemicellulose in the biomass to more simple sugars;
    wherein at least a portion of the hydrolyzing of cellulose and hemicellulose is performed by the genetically modified organism of claim 1.

* * * * *

UNITED STATES PATENT AND TRADEMARK OFFICE
CERTIFICATE OF CORRECTION

PATENT NO. : 8,492,114 B2
APPLICATION NO. : 12/587229
DATED : July 23, 2013
INVENTOR(S) : David N. Thompson et al.

It is certified that error appears in the above-identified patent and that said Letters Patent is hereby corrected as shown below:

On the title page:
In ITEM (75) Inventors:                                   change "Furnace, PA" to --PA Furnace, PA--
In ITEM (56) References Cited:
   OTHER PUBLICATIONS
     Page 2, $1^{st}$ column, $2^{nd}$ line of the
       $14^{th}$ entry (line 54),                    change "Quarlty" to --Quarterly--
     Page 2, $2^{nd}$ column, $2^{nd}$ line of the
       $1^{st}$ entry (line 2),                      change "Trands" to --Trends--
     Page 2, $2^{nd}$ column, $1^{st}$ line of the
       $15^{th}$ entry (line 31),                    change "Xylanaes," to --"Xylanase,--
     Page 2, $2^{nd}$ column, $1^{st}$ line of the
       $26^{th}$ entry (line 58),                    change "Functiona" to --Functional--
     Page 2, $2^{nd}$ column, $3^{rd}$ line of the
       $27^{th}$ entry (line 63),                    change "theremoacidophile" to --thermoacidophile--

In the specification:
   COLUMN 14, LINE 62,                              change "one of more" to --one or more--

Signed and Sealed this
Fifteenth Day of September, 2015

Michelle K. Lee
*Director of the United States Patent and Trademark Office*